(12) United States Patent
Zhang et al.

(10) Patent No.: US 12,358,891 B2
(45) Date of Patent: Jul. 15, 2025

(54) CRYSTALS OF QUINOLONE DERIVATIVES

(71) Applicant: CHIA TAI TIANQING PHARMACEUTICAL GROUP CO., LTD., Jiangsu (CN)

(72) Inventors: Xiquan Zhang, Lianyungang (CN); Shanchun Wang, Lianyungang (CN); Wenjun Geng, Lianyungang (CN); Yanlong Liu, Lianyungang (CN); Huihui Zhang, Lianyungang (CN); Fei Liu, Lianyungang (CN); Shanliang Zhu, Lianyungang (CN); Xinlu Li, Lianyungang (CN); Rui Zhao, Lianyungang (CN); Hongmei Gu, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 966 days.

(21) Appl. No.: 17/427,611

(22) PCT Filed: Jan. 31, 2020

(86) PCT No.: PCT/CN2020/074085
§ 371 (c)(1),
(2) Date: Jul. 30, 2021

(87) PCT Pub. No.: WO2020/156501
PCT Pub. Date: Aug. 6, 2020

(65) Prior Publication Data
US 2022/0098172 A1    Mar. 31, 2022

(30) Foreign Application Priority Data
Jan. 31, 2019    (CN) .......................... 201910095975.X

(51) Int. Cl.
| | | |
|---|---|---|
| C07D 401/12 | (2006.01) | |
| A61K 31/4709 | (2006.01) | |
| A61P 35/00 | (2006.01) | |

(52) U.S. Cl.
CPC ............ *C07D 401/12* (2013.01); *A61P 35/00* (2018.01); *C07B 2200/13* (2013.01)

(58) Field of Classification Search
CPC ... C07D 401/12; A61P 35/00; C07B 2200/13; A61K 31/4709
See application file for complete search history.

(56) References Cited

U.S. PATENT DOCUMENTS

| | | |
|---|---|---|
| 10,100,034 B2 | 10/2018 | Chen et al. |
| 10,183,017 B2 | 1/2019 | Zhang et al. |
| 10,251,876 B2 | 4/2019 | Wang et al. |

FOREIGN PATENT DOCUMENTS

| | | |
|---|---|---|
| CN | 102344438 A | 2/2012 |
| CN | 103664890 A | 3/2014 |

(Continued)

OTHER PUBLICATIONS

Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*

(Continued)

*Primary Examiner* — Jeffrey H Murray
*Assistant Examiner* — Kevin S Martin
(74) *Attorney, Agent, or Firm* — Maschoff Brennan

(57) ABSTRACT

The present application relates to the field of medicine, and relates to crystals of quinoline derivatives, and in particular, to crystals of a quinoline derivative anhydride and a solvate, as well as a method for preparing the crystals, pharmaceu- (Continued)

tical compositions containing the crystals, and a use thereof in the field of medicine. The present application further provides a preparation method therefor, which has a high yield, has mild crystallization conditions, is suitable for industrial production, and may better meet the needs of the pharmaceutical industry.

16 Claims, 9 Drawing Sheets

(56) References Cited

FOREIGN PATENT DOCUMENTS

| | | |
|---|---|---|
| CN | 103664892 A | 3/2014 |
| CN | 105213394 A | 1/2016 |
| CN | 105311029 A | 2/2016 |
| CN | 105311030 A | 2/2016 |
| CN | 107771078 A | 3/2018 |
| CN | 109748904 A | 5/2019 |
| CN | 110339195 A | 10/2019 |
| WO | 2008112407 | 9/2008 |
| WO | 2016179123 | 11/2016 |
| WO | 2019154273 A1 | 8/2019 |

OTHER PUBLICATIONS

Cecil Textbook of Medicine, 20th Ed, vol. 1, 1997 (Year: 1997).*
Gao Y, Liu P, Shi R. Anlotinib as a molecular targeted therapy for tumors. Oncol Lett. Aug. 2020;20(2):1001-1014. doi: 10.3892/ol.2020.11685. Epub May 28, 2020. PMID: 32724339; PMCID: PMC7377159. (Year: 2020).*

* cited by examiner

CRYSTALS OF QUINOLONE DERIVATIVES

CROSS-REFERENCE TO RELATED APPLICATIONS

The present application claims priority to and benefit of the Chinese Patent Application No. 201910095975.X, filed with National Intellectual Property Administration, PRC on Jan. 31, 2019, the disclosure of which is incorporated herein by reference in its entirety.

TECHNICAL FIELD

The present application relates to the technical field of pharmaceuticals, specifically to a crystalline form of a quinoline derivative, and more specifically to a crystalline form of an anhydrate or a solvate of a quinoline derivative 1-((4-(4-fluoro-2-methyl-1H-indol-5-yloxy)-6-methoxyquinolin-7-yloxy)methyl)cyclopropylamine, a method for preparing the crystalline form, a pharmaceutical composition comprising the crystalline form, and use thereof in the field of pharmaceuticals.

BACKGROUND

Tyrosine kinase is a group of enzymes which catalyze the phosphorylation of tyrosine residues in proteins. It plays an important role in intracellular signal transduction, takes part in adjustment, signaling and development of normal cells, and is closely related to proliferation, differentiation, migration and apoptosis of tumor cells. Many receptor tyrosine kinases are related to formation of tumor and can be classified as epidermal growth factor receptor (EGFR), platelet-derived growth factor receptor (PDGFR), vascular endothelial growth factor receptor (VEGFR), fibroblast growth factor receptor (FGFR) and the like according to the different structure of extracellular domain.

The compound 1-((4-(4-fluoro-2-methyl-1H-indol-5-yloxy)-6-methoxyquinolin-7-yloxy)methyl)cyclopropylamine and preparation methods thereof were first disclosed in Example 24 of Patent No. WO2008112407, which is shown in formula I:

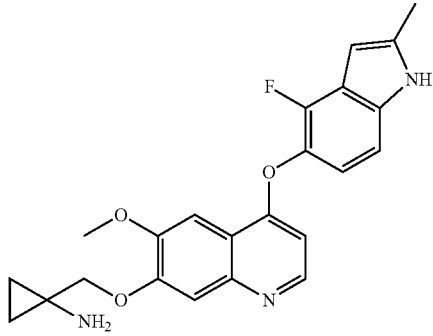

Formula I

The compound is a receptor tyrosine kinase inhibitor with multiple targets. It is capable of inhibiting the activity of kinases such as vascular endothelial growth factor receptors (VEGFR1, VEGFR2/KDR and VEGFR3), stem cell factor receptors, platelet-derived growth factor receptors and the like, and inhibiting downstream signaling mediated by VEGFR2, thereby inhibiting tumor angiogenesis.

Solid drugs are generally present in multiple crystalline forms, such as polymorphs, solvates (hydrates), salts, co-crystals, and the like. However, different crystalline forms of the same drug generally have different melting points, solubilities, stabilities, biological activities and the like, which are important factors influencing the preparation difficulty, the storage stability, the formulation difficulty, the bioavailability and the like. When a compound has multiple crystalline forms, since a drug of a certain crystalline form has specific thermodynamic properties and stability, in the preparation process, understanding the crystalline form of the compound in a dosage form is important for ensuring that the same form of the drug is applied in the manufacturing process. It is therefore necessary to ensure a compound in a single crystalline form or a known mixture of certain crystalline forms.

International Publication No. WO2016179123 discloses a crystalline form 1 of the free base of the compound of formula I and the preparation method thereof. Patent Application No. CN201010245688.1 discloses crystalline forms of an anhydrate or a dihydrate of a dihydrochloride salt of a quinoline derivative and preparation methods thereof.

The discovery of new crystalline forms of a pharmaceutical compound provides the opportunity to improve the physical properties of a drug, i.e., to extend the overall properties of the substance to provide better guidance to the studies of the compound and its formulation. Therefore, the crystalline form of the quinoline derivative and the pharmaceutical composition thereof disclosed herein are of commercial values in pharmaceutical manufacture and other applications.

SUMMARY

In one aspect, the present application provides a crystalline form (hereinafter referred to as crystalline form D) of an n-hexanol solvate of 1-((4-(4-fluoro-2-methyl-1H-indol-5-yloxy)-6-methoxyquinolin-7-yloxy)methyl) cyclopropylamine (compound of formula I), wherein in an X-ray powder diffraction (XRD) pattern using Cu-Kα radiation, the crystalline form D has diffraction peaks at 2θ in degree of about 7.28, 9.49, 10.07, 12.69, 14.97, 18.72, 19.26, 22.25, 22.58 and 24.02. For example, the crystalline form D has diffraction peaks at 2θ of 7.28, 9.49, 10.07, 12.69, 14.97, 18.72, 19.26, 22.25, 22.58 and 24.02±0.2°.

More specifically, the crystalline form D has diffraction peaks at 2θ in degree of about 7.28, 9.49, 10.07, 12.37, 12.69, 14.97, 15.66, 16.29, 17.25, 18.24, 18.72, 19.26, 21.15, 22.25, 22.58 and 24.02. For example, the crystalline form D has diffraction peaks at 2θ in degree of about 7.28, 9.49, 10.07, 12.37, 12.69, 14.97, 15.66, 16.29, 17.25, 18.24, 18.72, 19.26, 21.15, 22.25, 22.58 and 24.02±0.2°.

Still more specifically, the crystalline form D has diffraction peaks at 2θ in degree of about 7.28, 9.49, 10.07, 11.01, 12.37, 12.69, 14.97, 15.66, 16.29, 17.25, 18.24, 18.72, 19.26, 20.09, 20.77, 21.15, 22.25, 22.58, 23.59, 24.02, 24.88, 25.82, 26.29, 26.78, 27.48, 27.72, 28.71, 29.37, 29.85, 30.39, 30.67, 30.99, 31.37, 32.54, 32.92, 33.36, 34.05, 34.57, 35.47, 36.99, 37.37 and 37.62. For example, the crystalline form D has diffraction peaks at 2θ in degree of about 7.28, 9.49, 10.07, 11.01, 12.37, 12.69, 14.97, 15.66, 16.29, 17.25, 18.24, 18.72, 19.26, 20.09, 20.77, 21.15, 22.25, 22.58, 23.59, 24.02, 24.88, 25.82, 26.29, 26.78, 27.48, 27.72, 28.71, 29.37, 29.85, 30.39, 30.67, 30.99, 31.37, 32.54, 32.92, 33.36, 34.05, 34.57, 35.47, 36.99, 37.37 and 37.62±0.2°.

In some embodiments, the crystalline form D comprises n-hexanol in an amount of 5.0 to 21.0 wt %. In some specific embodiments, the crystalline form D comprises n-hexanol in an amount of 9.0 to 12.0 wt %. In some specific embodiments, the crystalline form D comprises n-hexanol in an amount of 10.0 to 11.5 wt %. In some specific embodiments, a crystalline form of a semi-n-hexanol solvate of the compound of formula I is provided.

In one specific embodiment, using Cu-Kα radiation, a typical XRD pattern of the crystalline form D is shown in FIG. 1, which has the following characteristics in Table 1:

TABLE 1

| Serial number | 2θ (°) | Relative intensity (%) |
|---|---|---|
| 1 | 7.28 | 5.1 |
| 2 | 9.49 | 20.1 |
| 3 | 10.07 | 10.3 |
| 4 | 11.01 | 0.8 |
| 5 | 12.37 | 4.4 |
| 6 | 12.69 | 11.5 |
| 7 | 13.44 | 0.5 |
| 8 | 14.97 | 45.1 |
| 9 | 15.66 | 17.7 |
| 10 | 16.29 | 7.4 |
| 11 | 17.25 | 5.9 |
| 12 | 18.24 | 12.6 |
| 13 | 18.72 | 100.0 |
| 14 | 19.26 | 42.1 |
| 15 | 20.09 | 2.8 |
| 16 | 20.77 | 1.8 |
| 17 | 21.15 | 14.8 |
| 18 | 22.25 | 73.3 |
| 19 | 22.58 | 84.8 |
| 20 | 23.59 | 2.4 |
| 21 | 24.02 | 59.4 |
| 22 | 24.88 | 2.3 |
| 23 | 25.82 | 6.8 |
| 24 | 26.29 | 0.9 |
| 25 | 26.78 | 6.2 |
| 26 | 27.48 | 2.0 |
| 27 | 27.72 | 1.5 |
| 28 | 28.71 | 1.9 |
| 29 | 29.37 | 5.3 |
| 30 | 29.85 | 5.1 |
| 31 | 30.39 | 7.9 |
| 32 | 30.67 | 4.4 |
| 33 | 30.99 | 2.1 |
| 34 | 31.37 | 2.6 |
| 35 | 32.54 | 0.9 |
| 36 | 32.92 | 3.0 |
| 37 | 33.36 | 4.5 |
| 38 | 34.05 | 1.4 |
| 39 | 34.57 | 0.7 |
| 40 | 35.47 | 1.4 |
| 41 | 36.99 | 2.0 |
| 42 | 37.37 | 2.8 |
| 43 | 37.62 | 2.3 |

In one specific embodiment, thermogravimetric-differential thermogravimetric (TG-DTG) pattern of the crystalline form D, as shown in FIG. 3, demonstrates a weight loss of 10.34 wt %.

In a second aspect, the present application provides a crystalline form (hereinafter referred to as crystalline form E) of 1-((4-(4-fluoro-2-methyl-1H-indol-5-yloxy)-6-methoxyquinolin-7-yloxy)methyl)cyclopropylamine (compound of formula I), wherein in an X-ray powder diffraction (XRD) pattern using Cu-Kα radiation, the crystalline form E has diffraction peaks at 2θ in degree of about 3.27, 6.56, 8.84, 9.95, 10.52, 13.10, 13.15, 15.58, 16.68, 17.84 and 18.66. For example, the crystalline form E has diffraction peaks at 2θ in degree of about 3.27, 6.56, 8.84, 9.95, 10.52, 13.10, 13.15, 15.58, 16.68, 17.84 and 18.66±0.2°.

More specifically, the crystalline form E has diffraction peaks at 2θ in degree of about 3.27, 6.56, 8.20, 8.84, 9.95, 10.52, 13.10, 13.15, 15.58, 16.68, 17.84, 18.66, 19.96, 20.19, 22.68, 23.12, 24.82, 25.37 and 27.22. For example, the crystalline form E has diffraction peaks at the following 2θ in degree of about 3.27, 6.56, 8.20, 8.84, 9.95, 10.52, 13.10, 13.15, 15.58, 16.68, 17.84, 18.66, 19.96, 20.19, 22.68, 23.12, 24.82, 25.37 and 27.22±0.2°.

Still more specifically, the crystalline form E has diffraction peaks at 2θ in degrees of about 3.27, 6.56, 7.20, 8.20, 8.84, 9.95, 10.52, 13.10, 13.15, 14.47, 15.58, 16.68, 17.84, 18.66, 19.96, 20.19, 20.94, 21.96, 22.68, 23.12, 24.82, 25.37, 27.22, 29.22, 31.39, 31.59, 33.93 and 35.02. For example, the crystalline form E has diffraction peaks at 2θ in degree of about 3.27, 6.56, 7.20, 8.20, 8.84, 9.95, 10.52, 13.10, 13.15, 14.47, 15.58, 16.68, 17.84, 18.66, 19.96, 20.19, 20.94, 21.96, 22.68, 23.12, 24.82, 25.37, 27.22, 29.22, 31.39, 31.59, 33.93, 35.02±0.2°.

In one specific embodiment, using Cu-Kα radiation, a typical XRD pattern of the crystalline form E is shown in FIG. 4, which has the following characteristics in Table 2:

TABLE 2

| Serial number | 2θ (°) | Relative intensity (%) |
|---|---|---|
| 1 | 3.27 | 92.7 |
| 2 | 6.56 | 55.5 |
| 3 | 7.20 | 2.9 |
| 4 | 8.20 | 15.0 |
| 5 | 8.84 | 88.3 |
| 6 | 9.95 | 100.0 |
| 7 | 10.52 | 78.5 |
| 8 | 13.10 | 29.3 |
| 9 | 13.15 | 28.4 |
| 10 | 14.47 | 2.4 |
| 11 | 15.58 | 30.7 |
| 12 | 16.68 | 58.1 |
| 13 | 17.84 | 60.1 |
| 14 | 18.66 | 65.5 |
| 15 | 19.96 | 13.2 |
| 16 | 20.19 | 13.5 |
| 17 | 20.94 | 25.1 |
| 18 | 21.96 | 9.0 |
| 19 | 22.68 | 61.0 |
| 20 | 23.12 | 60.9 |
| 21 | 24.82 | 31.4 |
| 22 | 25.37 | 42.5 |
| 23 | 27.22 | 32.2 |
| 24 | 29.22 | 7.3 |
| 25 | 31.39 | 2.3 |
| 26 | 31.59 | 4.8 |
| 27 | 33.93 | 2.4 |
| 28 | 35.02 | 3.2 |

In a third aspect, the present application provides a crystalline form (hereinafter referred to as crystalline form F) of a 1,4-dioxane solvate of 1-((4-(4-fluoro-2-methyl-1H-indol-5-yloxy)-6-methoxyquinolin-7-yloxy)methyl) cyclopropylamine (compound of formula I), wherein in an X-ray powder diffraction (XRD) pattern using Cu-Kα radiation, the crystalline form F has diffraction peaks at 2θ in degree of about 7.23, 9.48, 10.41, 13.34, 14.79, 18.03, 19.89, 22.45 and 23.50. For example, the crystalline form F has diffraction peaks at 2θ in degree of about 7.23, 9.48, 10.41, 13.34, 14.79, 18.03, 19.89, 22.45 and 23.50±0.2°.

More specifically, the crystalline form F has diffraction peaks at 2θ in degree of about 7.23, 9.48, 10.41, 11.04, 12.28, 13.34, 14.79, 15.00, 15.48, 16.17, 16.96, 17.49, 18.03, 19.58, 19.89, 21.34, 22.45, 23.50, 24.71, 25.04, 26.77 and 30.18. For example, the crystalline form F has diffraction peaks at 2θ in degree of about 7.23, 9.48, 10.41, 11.04, 12.28, 13.34, 14.79, 15.00, 15.48, 16.17, 16.96, 17.49, 18.03, 19.58, 19.89, 21.34, 22.45, 23.50, 24.71, 25.04, 26.77 and 30.18±0.2°.

Still more specifically, the crystalline form F has diffraction peaks at 2θ in degree of about 7.23, 9.48, 10.41, 11.04, 12.28, 13.34, 14.79, 15.00, 15.48, 16.17, 16.96, 17.49, 18.03, 19.16, 19.58, 19.89, 21.34, 22.45, 22.78, 23.50, 23.82, 23.99, 24.71, 25.04, 25.27, 25.63, 26.44, 26.77, 27.97, 28.69, 29.32, 30.18, 30.75, 31.26, 32.58, 33.03, 33.85, 34.26, 34.68, 36.31, 36.97, 37.70, 38.14 and 38.73. For example, the crystalline form F has diffraction peaks at 2θ in degree of about 7.23, 9.48, 10.41, 11.04, 12.28, 13.34, 14.79, 15.00, 15.48, 16.17, 16.96, 17.49, 18.03, 19.16, 19.58, 19.89, 21.34, 22.45, 22.78, 23.50, 23.82, 23.99, 24.71, 25.04, 25.27, 25.63, 26.44, 26.77, 27.97, 28.69, 29.32, 30.18, 30.75, 31.26, 32.58, 33.03, 33.85, 34.26, 34.68, 36.31, 36.97, 37.70, 38.14 and 38.73±0.2°.

In some embodiments, the crystalline form F comprises dioxane in an amount of 5.0 to 18.0 wt %. In some specific embodiments, the crystalline form F comprises dioxane in an amount of 7.0 to 12.0 wt %. In some specific embodiments, the crystalline form F comprises dioxane in an amount of 8.0 to 10.0 wt %.

In some specific embodiments, a crystalline form of a semi-dioxane solvate of the compound of formula I is provided.

In one specific embodiment, using Cu-Kα radiation, a typical XRD pattern of the crystalline form F is shown in FIG. 7, which has the following characteristics in Table 3:

TABLE 3

| Serial number | 2θ (°) | Relative intensity (%) |
|---|---|---|
| 1 | 7.23 | 9.7 |
| 2 | 9.48 | 10.4 |
| 3 | 10.41 | 8.0 |
| 4 | 11.04 | 1.1 |
| 5 | 12.28 | 5.3 |
| 6 | 13.34 | 26.5 |
| 7 | 14.79 | 33.0 |
| 8 | 15.00 | 12.5 |
| 9 | 15.48 | 9.1 |
| 10 | 16.17 | 3.7 |
| 11 | 16.96 | 15.1 |
| 12 | 17.49 | 3.0 |
| 13 | 18.03 | 100.0 |
| 14 | 19.16 | 3.6 |
| 15 | 19.58 | 9.6 |
| 16 | 19.89 | 36.8 |
| 17 | 21.34 | 7.1 |
| 18 | 22.45 | 41.8 |
| 19 | 22.78 | 6.0 |
| 20 | 23.50 | 73.3 |
| 21 | 23.82 | 7.4 |
| 22 | 23.99 | 4.1 |
| 23 | 24.71 | 15.9 |
| 24 | 25.04 | 8.3 |
| 25 | 25.27 | 4.6 |
| 26 | 25.63 | 2.8 |
| 27 | 26.44 | 1.6 |
| 28 | 26.77 | 8.1 |
| 29 | 27.97 | 1.2 |
| 30 | 28.69 | 3.4 |
| 31 | 29.32 | 0.8 |
| 32 | 30.18 | 7.9 |
| 33 | 30.75 | 3.0 |
| 34 | 31.26 | 1.0 |
| 35 | 32.58 | 1.0 |
| 36 | 33.03 | 3.1 |
| 37 | 33.85 | 2.4 |
| 38 | 34.26 | 2.3 |
| 39 | 34.68 | 2.5 |

TABLE 3-continued

| Serial number | 2θ (°) | Relative intensity (%) |
|---|---|---|
| 40 | 36.31 | 1.5 |
| 41 | 36.97 | 0.7 |
| 42 | 37.70 | 2.5 |
| 43 | 38.14 | 1.8 |
| 44 | 38.73 | 1.1 |

In one specific embodiment, thermogravimetric-differential thermogravimetric (TG-DTG) pattern of crystalline form F, as shown in FIG. 9, demonstrates a weight loss of 9.18 wt %.

In a fourth aspect, the present application provides a crystalline form (hereinafter referred to as crystalline form G) of an acetone solvate of 1-(((4-(4-fluoro-2-methyl-1H-indol-5-yloxy)-6-methoxyquinolin-7-yloxy)methyl) cyclopropylamine (compound of formula I), wherein in an X-ray powder diffraction (XRD) pattern using Cu-Kα radiation, the crystalline form G has diffraction peaks at 2θ in degree of about 7.21, 8.94, 9.58, 10.81, 14.65, 15.18, 16.82, 17.54, 18.16, 19.93, 20.60, 22.16, 24.17, 24.91, 27.54 and 27.59. For example, the crystalline form G has diffraction peaks at 2θ in degree of about 7.21, 8.94, 9.58, 10.81, 14.65, 15.18, 16.82, 17.54, 18.16, 19.93, 20.60, 22.16, 24.17, 24.91, 27.54 and 27.59±0.2°.

More specifically, the crystalline form G has diffraction peaks at 2θ in degree of about 7.21, 8.94, 9.58, 10.81, 13.07, 14.65, 15.18, 16.82, 17.54, 18.16, 18.88, 19.93, 20.60, 21.02, 22.16, 24.17, 24.91, 25.81, 27.54, 27.59, 29.16 and 29.75. For example, the crystalline form G has diffraction peaks at 2θ in degree of about 7.21, 8.94, 9.58, 10.81, 13.07, 14.65, 15.18, 16.82, 17.54, 18.16, 18.88, 19.93, 20.60, 21.02, 22.16, 24.17, 24.91, 25.81, 27.54, 27.59, 29.16 and 29.75±0.2°.

Still more specifically, the crystalline form G has diffraction peaks at 2θ in degree of about 7.21, 8.94, 9.58, 10.40, 10.81, 12.69, 13.07, 14.65, 15.18, 15.42, 16.82, 17.54, 18.16, 18.88, 19.35, 19.93, 20.60, 21.02, 21.70, 22.16, 24.17, 24.91, 25.81, 27.54, 27.59, 28.10, 29.16, 29.75, 30.37, 30.93, 31.68, 32.51, 33.18, 33.82, 35.83, 36.40, 37.39, 38.42 and 39.49. For example, the crystalline form G has diffraction peaks at 2θ in degree of about 7.21, 8.94, 9.58, 10.40, 10.81, 12.69, 13.07, 14.65, 15.18, 15.42, 16.82, 17.54, 18.16, 18.88, 19.35, 19.93, 20.60, 21.02, 21.70, 22.16, 24.17, 24.91, 25.81, 27.54, 27.59, 28.10, 29.16, 29.75, 30.37, 30.93, 31.68, 32.51, 33.18, 33.82, 35.83, 36.40, 37.39, 38.42 and 39.49±0.2°.

In some embodiments, the crystalline form G comprises acetone in an amount of 2.0 to 13.0 wt %. In some specific embodiments, the crystalline form G comprises acetone in an amount of 3.0 to 6.0 wt %. In some specific embodiments, the crystalline form G comprises acetone in an amount of 4.0 to 5.0 wt %.

In some specific embodiments, a crystalline form of a mono-acetone solvate of the compound of formula I is provided. In one specific embodiment, the present application provides a crystalline form of the acetone solvate of the compound of formula I comprising IA moles of acetone.

In one specific embodiment, using Cu-Kα radiation, a typical XRD pattern of the crystalline form G is shown in FIG. 10, which has the following characteristics in Table 4:

TABLE 4

| Serial number | 2θ (°) | Relative intensity (%) |
|---|---|---|
| 1 | 7.21 | 4.9 |
| 2 | 8.94 | 7.5 |
| 3 | 9.58 | 12.6 |
| 4 | 10.40 | 1.6 |
| 5 | 10.81 | 13.0 |
| 6 | 12.69 | 0.9 |
| 7 | 13.07 | 3.4 |
| 8 | 14.65 | 15.3 |
| 9 | 15.18 | 24.9 |
| 10 | 15.42 | 4.5 |
| 11 | 16.82 | 26.5 |
| 12 | 17.54 | 33.7 |
| 13 | 18.16 | 100.0 |
| 14 | 18.88 | 8.0 |
| 15 | 19.35 | 17.3 |
| 16 | 19.93 | 3.7 |
| 17 | 20.60 | 18.0 |
| 18 | 21.02 | 4.3 |
| 19 | 21.70 | 5.1 |
| 20 | 22.16 | 85.9 |
| 21 | 24.17 | 48.7 |
| 22 | 24.91 | 20.3 |
| 23 | 25.81 | 2.3 |
| 24 | 27.54 | 26.8 |
| 25 | 27.59 | 24.9 |
| 26 | 28.10 | 2.8 |
| 27 | 29.16 | 12.4 |
| 28 | 29.75 | 10.6 |
| 29 | 30.37 | 5.3 |
| 30 | 30.93 | 0.8 |
| 31 | 31.68 | 1.6 |
| 32 | 32.51 | 1.0 |
| 33 | 33.18 | 2.7 |
| 34 | 33.82 | 1.9 |
| 35 | 35.83 | 0.7 |
| 36 | 36.40 | 1.3 |
| 37 | 37.39 | 1.3 |
| 38 | 38.42 | 1.9 |
| 39 | 39.49 | 0.7 |

In one specific embodiment, thermogravimetric-differential thermogravimetric (TG-DTG) pattern of crystalline form G, as shown in FIG. 12, demonstrates a weight loss of 4.68 wt %.

In a fifth aspect, the present application provides a crystalline form (hereinafter referred to as crystalline form H) of an ethyl acetate solvate of 1-((4-(4-fluoro-2-methyl-1H-indol-5-yloxy)-6-methoxyquinolin-7-yloxy)methyl) cyclopropylamine (compound of formula I), wherein in an X-ray powder diffraction (XRD) pattern using Cu-Kα radiation, the crystalline form H has diffraction peaks at 2θ in degree of about 7.48, 9.71, 10.70, 12.52, 13.30, 13.51, 15.08, 15.65, 17.08, 18.47, 20.15, 21.63, 22.77 and 23.84. For example, the crystalline form H has diffraction peaks at 2θ in degree of about 7.48, 9.71, 10.70, 12.52, 13.30, 13.51, 15.08, 15.65, 17.08, 18.47, 20.15, 21.63, 22.77 and 23.84±0.2°.

More specifically, the crystalline form H has diffraction peaks at 2θ in degree of about 7.48, 9.71, 9.98, 10.70, 12.52, 13.30, 13.51, 15.08, 15.65, 17.08, 17.75, 18.47, 19.57, 20.15, 21.63, 22.77, 23.31, 23.84, 24.85, 25.26, 25.79, 26.19, 26.93, 29.11, 29.65 and 30.36. For example, the crystalline form H has diffraction peaks at 2θ in degree of about 7.48, 9.71, 9.98, 10.70, 12.52, 13.30, 13.51, 15.08, 15.65, 17.08, 17.75, 18.47, 19.57, 20.15, 21.63, 22.77, 23.31, 23.84, 24.85, 25.26, 25.79, 26.19, 26.93, 29.11, 29.65 and 30.36±0.2°.

Still more specifically, the crystalline form H has diffraction peaks at 2θ in degree of about 7.48, 9.71, 9.98, 10.70, 12.52, 13.30, 13.51, 15.08, 15.65, 16.70, 17.08, 17.75, 18.47, 19.56, 19.57, 20.15, 21.63, 22.77, 23.31, 23.64, 23.84, 24.13, 24.85, 25.26, 25.79, 26.19, 26.93, 27.84, 28.08, 29.11, 29.65, 30.36, 31.02, 32.97, 33.35, 33.38, 34.48, 36.30, 36.64, 37.93, 38.97 and 39.74. For example, the crystalline form H has diffraction peaks at 2θ in degree of about 7.48, 9.71, 9.98, 10.70, 12.52, 13.30, 13.51, 15.08, 15.65, 16.70, 17.08, 17.75, 18.47, 19.56, 19.57, 20.15, 21.63, 22.77, 23.31, 23.64, 23.84, 24.13, 24.85, 25.26, 25.79, 26.19, 26.93, 27.84, 28.08, 29.11, 29.65, 30.36, 31.02, 32.97, 33.35, 33.38, 34.48, 36.30, 36.64, 37.93, 38.97 and 39.74±0.2°.

In some embodiments, the crystalline form H comprises ethyl acetate in an amount of 5.0 to 18.0 wt %. In some specific embodiments, the crystalline form H comprises ethyl acetate in an amount of 7.0 to 12.0 wt %. In some specific embodiments, the crystalline form H comprises ethyl acetate in an amount of 9.0 to 10.0 wt %.

In some specific embodiments, a crystalline form of a mono-ethyl acetate solvate of the compound of formula I is provided. In some specific embodiments, a crystalline form of a semi-ethyl acetate solvate of the compound of formula I is provided.

In one specific embodiment, using Cu-Kα radiation, a typical XRD pattern of the crystalline form H is shown in FIG. 13, which has the following characteristics in Table 5:

TABLE 5

| Serial number | 2θ (°) | Relative intensity (%) |
|---|---|---|
| 1 | 7.48 | 28.2 |
| 2 | 9.71 | 9.4 |
| 3 | 9.98 | 3.1 |
| 4 | 10.70 | 12.8 |
| 5 | 12.52 | 7.1 |
| 6 | 13.30 | 34.4 |
| 7 | 13.51 | 36.7 |
| 8 | 15.08 | 74.7 |
| 9 | 15.65 | 25.9 |
| 10 | 16.70 | 7.0 |
| 11 | 17.08 | 21.3 |
| 12 | 17.75 | 11.1 |
| 13 | 18.47 | 100.0 |
| 14 | 19.56 | 16.7 |
| 15 | 19.57 | 16.6 |
| 16 | 20.15 | 79.3 |
| 17 | 21.63 | 16.5 |
| 18 | 22.77 | 81.9 |
| 19 | 23.31 | 24.7 |
| 20 | 23.64 | 46.7 |
| 21 | 23.84 | 70.7 |
| 22 | 24.13 | 9.6 |
| 23 | 24.85 | 24.4 |
| 24 | 25.26 | 13.3 |
| 25 | 25.79 | 6.2 |
| 26 | 26.19 | 5.1 |
| 27 | 26.93 | 17.3 |
| 28 | 27.84 | 2.7 |
| 29 | 28.08 | 1.2 |
| 30 | 29.11 | 5.7 |
| 31 | 29.65 | 1.3 |
| 32 | 30.36 | 16.4 |
| 33 | 31.02 | 3.8 |
| 34 | 32.97 | 5.1 |
| 35 | 33.35 | 5.5 |
| 36 | 33.38 | 5.1 |
| 37 | 34.48 | 4.1 |
| 38 | 36.30 | 1.9 |
| 39 | 36.64 | 0.9 |
| 40 | 37.93 | 5.9 |
| 41 | 38.97 | 4.1 |
| 42 | 39.74 | 1.6 |

In one specific embodiment, thermogravimetric-differential thermogravimetric (TG-DTG) pattern of crystalline form H, as shown in FIG. 15, demonstrates a weight loss of 9.24 wt %.

In a sixth aspect, the present application provides a crystalline form (hereinafter referred to as crystalline form J) of a tetrahydrofuran solvate of 1-((4-(4-fluoro-2-methyl-1H-indol-5-yloxy)-6-methoxyquinolin-7-yloxy)methyl) cyclopropylamine (compound of formula I), wherein in an X-ray powder diffraction (XRD) pattern using Cu-Kα radiation, the crystalline form J has diffraction peaks at 2θ in degree of about 7.27, 9.75, 10.15, 10.44, 12.38, 14.60, 15.16, 15.50, 18.01, 18.37, 19.60, 21.99, 24.20 and 29.49. For example, the crystalline form J has diffraction peaks at 2θ in degree of about 7.27, 9.75, 10.15, 10.44, 12.38, 14.60, 15.16, 15.50, 18.01, 18.37, 19.60, 21.99, 24.20 and 29.49±0.2°.

More specifically, the crystalline form J has diffraction peaks at 2θ in degree of about 7.27, 9.75, 12.38, 14.60, 15.16, 15.50, 18.01, 18.37, 19.60, 21.68, 21.99, 22.56, 22.82, 24.20, 24.95, 25.44, 27.04, 27.67, 28.67, 29.15, 29.49 and 37.82. For example, the crystalline form J has diffraction peaks at 2θ in degree of about 7.27, 9.75, 12.38, 14.60, 15.16, 15.50, 18.01, 18.37, 19.60, 21.68, 21.99, 22.56, 22.82, 24.20, 24.95, 25.44, 27.04, 27.67, 28.67, 29.15, 29.49 and 37.82±0.2°.

Still more specifically, the crystalline form J has diffraction peaks at 2θ in degree of about 7.27, 9.75, 10.15, 10.44, 12.38, 14.60, 15.16, 15.50, 16.68, 17.39, 18.01, 18.37, 19.43, 19.60, 20.14, 20.52, 20.95, 21.41, 21.68, 21.99, 22.56, 22.82, 23.30, 24.06, 24.20, 24.95, 25.44, 25.73, 27.04, 27.67, 28.53, 28.67, 29.15, 29.49, 30.10, 30.32, 30.66, 32.10, 32.40, 33.86, 34.95, 36.22, 36.44, 37.02 and 37.82. For example, the crystalline form J has diffraction peaks at 2θ in degree of about 7.27, 9.75, 10.15, 10.44, 12.38, 14.60, 15.16, 15.50, 16.68, 17.39, 18.01, 18.37, 19.43, 19.60, 20.14, 20.52, 20.95, 21.41, 21.68, 21.99, 22.56, 22.82, 23.30, 24.06, 24.20, 24.95, 25.44, 25.73, 27.04, 27.67, 28.53, 28.67, 29.15, 29.49, 30.10, 30.32, 30.66, 32.10, 32.40, 33.86, 34.95, 36.22, 36.44, 37.02 and 37.82±0.2°.

In some embodiments, the crystalline form J comprises tetrahydrofuran in an amount of 10.0 to 18.0 wt %. In some specific embodiments, the crystalline form J comprises tetrahydrofuran in an amount of 12.0 to 17.0 wt %. In some specific embodiments, the crystalline form J comprises tetrahydrofuran in an amount of 13.0 to 16.0 wt %. In some specific embodiments, a crystalline form of a mono-tetrahydrofuran solvate of the compound of formula I is provided.

In one specific embodiment, using Cu-Kα radiation, a typical XRD pattern of the crystalline form J is shown in FIG. 16, which has the following characteristics in Table 6:

TABLE 6

| Serial number | 2θ (°) | Relative intensity (%) |
|---|---|---|
| 1 | 7.27 | 10.6 |
| 2 | 9.75 | 24.2 |
| 3 | 10.15 | 2.4 |
| 4 | 10.44 | 1.0 |
| 5 | 12.38 | 17.5 |
| 6 | 14.60 | 24.7 |
| 7 | 15.16 | 13.4 |
| 8 | 15.50 | 23.0 |
| 9 | 16.68 | 1.5 |
| 10 | 17.39 | 1.9 |
| 11 | 18.01 | 16.9 |
| 12 | 18.37 | 27.6 |
| 13 | 19.43 | 20.9 |
| 14 | 19.60 | 53.5 |
| 15 | 20.14 | 0.4 |
| 16 | 20.52 | 0.4 |
| 17 | 20.95 | 1.1 |
| 18 | 21.41 | 4.4 |
| 19 | 21.68 | 15.1 |
| 20 | 21.99 | 100.0 |
| 21 | 22.56 | 7.9 |
| 22 | 22.82 | 4.4 |
| 23 | 23.30 | 0.2 |
| 24 | 24.06 | 6.0 |
| 25 | 24.20 | 20.1 |
| 26 | 24.95 | 5.2 |
| 27 | 25.44 | 3.2 |
| 28 | 25.73 | 0.6 |
| 29 | 26.25 | 0.2 |
| 30 | 27.04 | 4.1 |
| 31 | 27.67 | 1.1 |
| 32 | 28.53 | 2.0 |
| 33 | 28.67 | 4.5 |
| 34 | 29.15 | 2.5 |
| 35 | 29.49 | 17.3 |
| 36 | 30.10 | 1.7 |
| 37 | 30.32 | 1.9 |
| 38 | 30.66 | 2.8 |
| 39 | 32.10 | 1.4 |
| 40 | 32.40 | 3.5 |
| 41 | 33.51 | 0.5 |
| 42 | 33.57 | 0.4 |
| 43 | 33.86 | 0.6 |
| 44 | 34.95 | 1.6 |
| 45 | 35.81 | 0.2 |
| 46 | 36.22 | 1.7 |
| 47 | 36.44 | 4.1 |
| 48 | 37.02 | 1.4 |
| 49 | 37.82 | 6.4 |
| 50 | 38.42 | 0.4 |
| 51 | 39.26 | 0.3 |

In one specific embodiment, thermogravimetric-differential thermogravimetric (TG-DTG) pattern of crystalline form J, as shown in FIG. 18, demonstrates a weight loss of 13.22 wt %.

In another aspect, the present application provides methods for preparing the crystalline form D, the crystalline form E, the crystalline form F, the crystalline form G, the crystalline form H and the crystalline form J above.

In some embodiments, provided is a method for preparing the crystalline form D of the compound of formula I, comprising mixing the compound of formula I with n-hexanol at 25° C., and crystallizing by suspension to obtain the crystalline form D.

In some embodiments, provided is a method for preparing the crystalline form E of the compound of formula I, comprising mixing the compound of formula I with paraxylene, and crystallizing by cooling to obtain the crystalline form E.

In some embodiments, further provided is a method for preparing the crystalline form E of the compound of formula I, comprising mixing the compound of formula I with paraxylene at 25° C., and crystallizing by suspension to obtain the crystalline form E. In some embodiments, provided is a method for preparing the crystalline form E of the compound of formula I, comprising mixing the compound of formula I with paraxylene at 50° C., and crystallizing by suspension to obtain the crystalline form E.

In some embodiments, provided is a method for preparing the crystalline form F of the compound of formula I, comprising mixing the compound of formula I with dioxane, and crystallizing by suspension to obtain the crystalline form F.

In some embodiments, provided is a method for preparing the crystalline form F of the compound of formula I, comprising mixing the compound of formula I with dioxane at 25° C., and crystallizing by suspension to obtain the crystalline form F. In some embodiments, provided is a method for preparing the crystalline form F of the compound of formula I, comprising mixing the compound of formula I with dioxane at 50° C., and crystallizing by suspension to obtain the crystalline form F.

In some embodiments, provided is a method for preparing the crystalline form G of the compound of formula I, comprising crystallizing the compound of formula I by suspension in acetone to obtain the crystalline form G.

In some embodiments, further provided is a method for preparing the crystalline form G of the compound of formula I, comprising mixing the compound of formula I with acetone at 25° C., and crystallizing by suspension to obtain the crystalline form G. In some embodiments, provided is a method for preparing the crystalline form G of the compound of formula I, comprising mixing the compound of formula I with acetone at 50° C., and crystallizing by suspension to obtain the crystalline form G.

In some embodiments, provided is a method for preparing the crystalline form H of the compound of formula I, comprising mixing the compound of formula I with ethyl acetate, and crystallizing by suspension to obtain the crystalline form H.

In some embodiments, provided is a method for preparing the crystalline form J of the compound of formula I, comprising mixing the compound of formula I with tetrahydrofuran, and crystallizing by suspension to obtain the crystalline form J.

The crystallizing by suspension described in the present application comprises: adding a proper amount of the compound of formula I into a solvent, and stirring for equilibration at a certain temperature for 24 hours; in some embodiments, the stirring for equilibration is performed at 25° C., or in some embodiments, the stirring for equilibration is performed at 50° C.; and then centrifuging the solution, and drying the solid at 45-50° C.

The crystallizing by cooling described in the present application comprises: mixing a proper amount of the compound of formula I with a solvent, and stirring and heating the mixture until completely dissolved, wherein in some embodiments, the mixture is heated to 60° C. until completely dissolved; cooling the solution to 15° C. for crystallization; filtering the mixture; and drying the filter residues to obtain a crystalline form. If desired, the undissolved compound of formula I can be removed by filtration to obtain a clear solution.

The crystallizing by evaporation described in the present application comprises: mixing a proper amount of the compound of formula I with a solvent, and stirring and heating the mixture until completely dissolved, wherein in some embodiments, the mixture is heated to 60° C.; transferring the clear solution into a sample bottle; slowly evaporating the solvent at room temperature for crystallization; collecting and drying the residues to obtain a crystalline form. If desired, the undissolved compound of formula I can be removed by filtration to obtain a clear solution.

If desired, activated carbon can be added and the resultant mixture can be filtered before crystallization; the crystallization can be promoted by conventional methods such as stirring, adding seed crystals or stewing. The crystals may be further washed with an organic solvent (e.g., petroleum ether, isopropyl ether, methyl tert-butyl ether, n-heptane or n-hexane) when separating the crystalline form.

In still another aspect, the present application provides crystalline compositions comprising the crystalline form D, the crystalline form E, the crystalline form F, the crystalline form G, the crystalline form H or the crystalline form J above. The crystalline composition comprising the crystalline form D refers to a composition in which the crystalline form D consists of 50% or more, preferably 70% or more, more preferably 90% or more, and most preferably 95% or more of the composition by weight. The composition may further comprise small amounts of other crystalline forms or an amorphous form of the compound of formula I.

The crystalline composition comprising the crystalline form E refers to a composition in which the crystalline form E consists of 50% or more, preferably 70% or more, more preferably 90% or more, and most preferably 95% or more of the composition by weight. The composition may further comprise small amounts of other crystalline forms or an amorphous form of the compound of formula I.

The crystalline composition comprising the crystalline form F refers to a composition in which the crystalline form F consists of 50% or more, preferably 70% or more, more preferably 90% or more, and most preferably 95% or more of the composition by weight. The composition may further comprise small amounts of other crystalline forms or an amorphous form of the compound of formula I.

The crystalline composition comprising the crystalline form G refers to a composition in which the crystalline form G consists of 50% or more, preferably 70% or more, more preferably 90% or more, and most preferably 95% or more of the composition by weight. The composition may further comprise small amounts of other crystalline forms or an amorphous form of the compound of formula I.

The crystalline composition comprising the crystalline form H refers to a composition in which the crystalline form H consists of 50% or more, preferably 70% or more, more preferably 90% or more, and most preferably 95% or more of the composition by weight. The composition may further comprise small amounts of other crystalline forms or an amorphous form of the compound of formula I.

The crystalline composition comprising the crystalline form J refers to a composition in which the crystalline form J consists of 50% or more, preferably 70% or more, more preferably 90% or more, and most preferably 95% or more of the composition by weight. The composition may further comprise small amounts of other crystalline forms or an amorphous form of the compound of formula I.

The crystalline form D or crystalline composition comprising the crystalline form D, the crystalline form E or crystalline composition comprising the crystalline form E, the crystalline form F or crystalline composition comprising the crystalline form F, the crystalline form G or crystalline composition comprising the crystalline form G, the crystalline form H or crystalline composition comprising the crystalline form H, or the crystalline form J or crystalline composition comprising the crystalline form J described herein are collectively referred to as the "active substance according to the present application" hereinafter.

The active substance of the present application may be administered by any route suitable for the target conditions, including oral, topical (e.g., buccal, sublingual, etc.), parenteral (e.g., subcutaneous, intramuscular, intravenous, intraspinal, intradermal, intrathecal, etc.), rectal, vaginal, and other routes. The preferred route of administration is oral administration.

Although the active substance of the present application can be administered in the form of a pure substance, they are generally administered in the form of a pharmaceutical composition. The pharmaceutical composition comprising the active substance according to the present application further comprises one or more pharmaceutically acceptable excipients, and optionally, other therapeutically active ingredients. It can also be administered in combination with chemotherapy, radiotherapy, or surgery.

Pharmaceutical compositions suitable for oral administration include tablets, capsules, powders, granules, dripping pills, pastes, pulvis, tinctures, and the like, preferably tablets and capsules. The tablet may be a common tablet, dispersible tablet, effervescent tablet, sustained-release tablet, controlled-release tablet or enteric coated tablet. The capsule may be a common capsule, sustained-release capsule, controlled-release capsule or enteric coated capsule.

The pharmaceutical composition of the present application can be prepared by a conventional method using a conventional pharmaceutical excipient known in the art. Conventional pharmaceutic excipients include fillers, absorbents, wetting agents, binders, disintegrants, lubricants and the like. The fillers include starch, lactose, mannitol, microcrystalline cellulose, and the like. The absorbents include calcium sulfate, calcium hydrogen phosphate, calcium carbonate, magnesium oxide and the like. The wetting agents include water, ethanol, and the like. The binders include hydroxypropyl methylcellulose, polyvidone, microcrystalline cellulose, and the like. The disintegrants include croscarmellose sodium, crospovidone, surfactants, low-substituted hydroxypropyl cellulose, and the like. The lubricants include magnesium stearate, talcum powder, polyethylene glycol, magnesium dodecyl sulfate, silia gel micropowder, talcum powder, and the like. The pharmaceutically acceptable carrier further includes coloring agents, sweeteners and the like.

In a unit formulation of tablets and capsules for oral administration, the amount of the active substance according to the present application shall be necessarily changed according to the treatment condition and the specific route of administration of a subject. For example, a unit formulation for oral administration may conveniently comprises, for example, 1 mg to 100 mg of the active substance, preferably 3 mg to 30 mg of the active substance.

The active substance according to the present application and the pharmaceutical composition thereof have activity in inhibiting receptor tyrosine kinase, and can be used for treating tumors, such as liver cancer, kidney cancer, colon cancer, gastrointestinal stromal tumor, soft tissue sarcoma, gastric cancer, medullary thyroid cancer, esophageal squamous cell carcinoma, small-cell lung cancer, non-small cell lung cancer, endometrial cancer, ovarian cancer, cervical cancer, and fallopian tube cancer.

In another aspect, the present application provides use of the crystalline form D, the crystalline form E, the crystalline form F, the crystalline form G, the crystalline form H or the crystalline form J of the compound of formula I, the crystalline composition thereof or the pharmaceutical composition thereof in preparing a medicament for treating a tumor.

In another aspect, the present application provides a method of treating a tumor comprising administering to a subject in need a therapeutically effective amount of the crystalline form D, the crystalline form E, the crystalline form F, the crystalline form G, the crystalline form H or the crystalline form J of the compound of formula I, the crystalline composition thereof or the pharmaceutical composition thereof.

In another aspect, the present application provides the crystalline form D, the crystalline form E, the crystalline form F, the crystalline form G, the crystalline form H or the crystalline form J of the compound of formula I, the crystalline composition thereof or the pharmaceutical composition thereof for treating a tumor in a subject in need.

In some embodiments of the present application, the subject is a mammal, e.g., a human.

It should be noted that in X-ray diffraction (XRD), the diffraction pattern acquired from a crystal compound described herein is generally characteristic for a particular crystalline, where the relative intensities of the bands may vary due to dominant orientation effects arising from differences in crystallization conditions, particle sizes, and other measurement conditions. Therefore, the relative intensities of the diffraction peaks are not characteristic for the crystal concerned, and it is important to consider the relative positions of the peaks rather than their relative intensities for determining whether it is the same as a known crystal. In addition, there may be slight errors in the position of the peaks for any given crystal, as is also well known in the field of crystallography. For example, the position of the peak may shift due to temperature changes, sample movement or calibration of the instrument when analyzing a sample, and the error in the determination of 2θ value is typically about ±0.2°. Therefore, this error should be considered when determining a crystal structure. In XRD pattern, the peak position is usually represented by 2θ angle or crystal plane distance d, and there is a simple conversion relationship between the two: d=λ/sin θ, wherein d represents the crystal plane distance, λ represents the wavelength of the incident X-ray, and θ is the diffraction angle.

The transition temperature is determined by differential scanning calorimetry (DSC) when a crystalline form absorbs or releases heat due to a change in the crystalline structure or melting of the crystalline form. For the same crystalline form of the same compound, the thermal transition temperature and melting point errors in continuous analyses are typically within about 5° C., usually within about 3° C., and a compound having a given DSC peak or melting point means that the DSC peak or melting point is ±5° C. DSC provides an auxiliary method to identify different crystalline forms. Different crystalline morphologies can be identified by their different transition temperatures. It should be noted that for a mixture, its DSC peak or melting point may vary over a larger range.

Furthermore, melting temperature is closely related to heating rate due to the decomposition of a substance in the melting process.

"Mammal" includes human, domestic animals such as laboratory mammals and domestic pets (e.g., cat, dog, pig, cow, sheep, goat, horse, rabbit), and non-domesticated mammals such as wild mammals.

The term "pharmaceutical composition" refers to a formulation of the compound disclosed herein with a vehicle commonly recognized in the art for delivering a biologically active compound to a mammal, such as a human. The vehicle includes all pharmaceutically acceptable carriers for its use. The pharmaceutical composition facilitates administration of the compound to an organism.

The term "therapeutically effective amount" refers to an amount of a drug or a medicament that is sufficient to provide the desired effect but is non-toxic. The determination of the effective amount varies from person to person, depending on the age and general condition of a subject and also depending on the particular active substance. The appropriate effective amount in a case may be determined by those skilled in the art in the light of routine tests.

The term "pharmaceutically acceptable carriers" refers to those which are administered together with the active ingredient, do not have a significant irritating effect on an organism and do not impair the biological activity and properties of the active compound. For additional information on carriers, reference may be made to Remington: The Science and Practice of Pharmacy, 21st Ed., Lippincott, Williams & Wilkins (2005), the content of which is incorporated herein by reference.

As used herein, unless otherwise stated, the terms "comprise", "comprises" and "comprising" or equivalents thereof are open-ended statements and mean that elements, components and steps that are not specified may be included in addition to those listed.

All patents, patent applications and other identified publications are expressly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates of these documents or the contents of these documents. Moreover, in any country or region, any reference to these publications herein is not to be construed as an admission that the publications form part of the commonly recognized knowledge in the art.

The crystalline form disclosed herein has the advantages of high purity, high crystallinity, good stability, low hygroscopicity, good fluidity and the like, and characteristics of improved bioavailability, improved stability and solubility, accelerated dissolution and the like, which make the crystalline form more suitable for pharmacy. The present application further provides a method for preparing the crystalline form, which is characterized by high yield and mild crystallization conditions, is suitable for industrial production and can better meet the needs of the pharmaceutical industry.

DETAILED DESCRIPTION

The following specific examples are intended to allow those skilled in the art to clearly understand and implement the present application. These specific examples should not be considered as limiting the scope of the present application, but merely as being exemplary description and representative of the present application.

The technical solutions of the present application will be described with specific examples, but the scope of the present application is not limited to the scope of the following examples. The reagents used are all commercially available products.

The instrument and method for data acquisition:

X-ray powder diffraction (XRD) spectroscopy was performed in the following conditions: scanning range of 2θ value: 2-35°; step size: 0.02; time: 0.2 seconds; rotation speed: 30 n/min; target tube: Cu; voltage: 30 kV; current: 10 mA.

Differential scanning calorimetry (DSC) was performed in the following conditions: temperature: 40-300° C.; scanning speed: 10° C./min.

Thermogravimetric analysis (TGA) was performed in the following conditions: temperature: 30-300° C.; scanning speed: 10° C./min.

The differential thermogravimetric (DTG) pattern is the first order differential TG curve versus temperature. In the condition of constant temperature rise, the relationship between the rate of weight loss of the sample and the temperature was measured.

The method for moisture content measurement was Karl Fischer titration.

The compounds of formula I described in the present application can be prepared with reference to Example 24 of WO2008112407.

Example 1. Preparation of Crystalline Form D of Compound of Formula I

Figure 1:
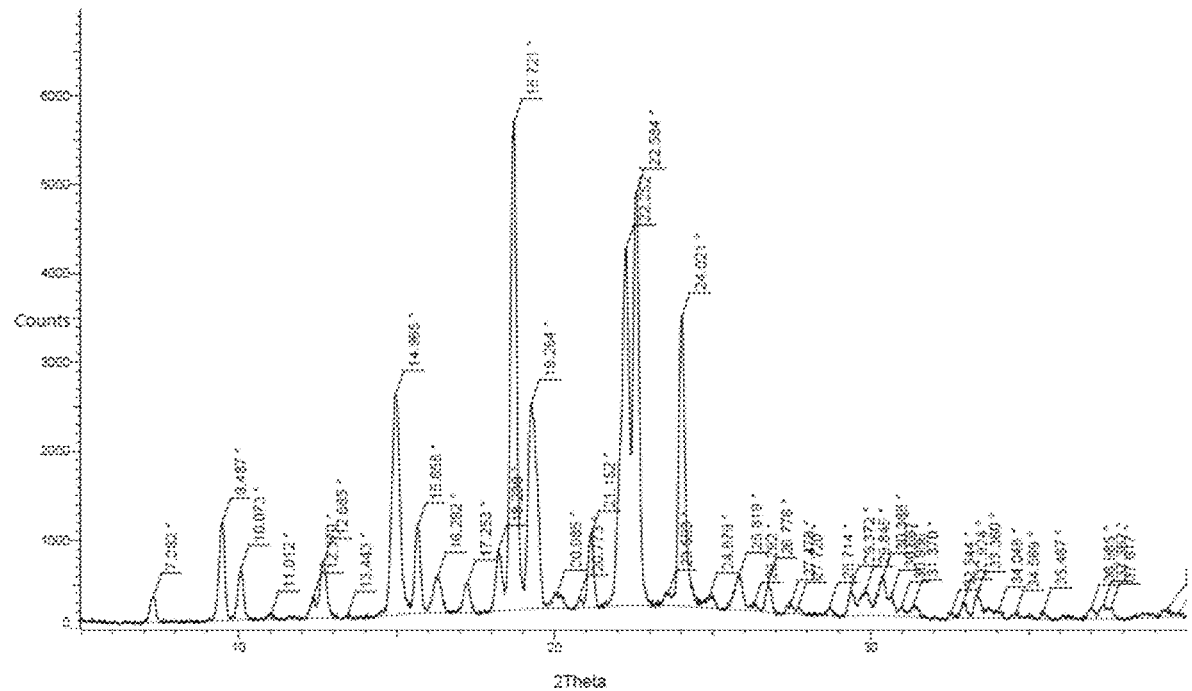
FIG. 1 illustrates an XRD pattern of the crystalline form D.
Figure 2:
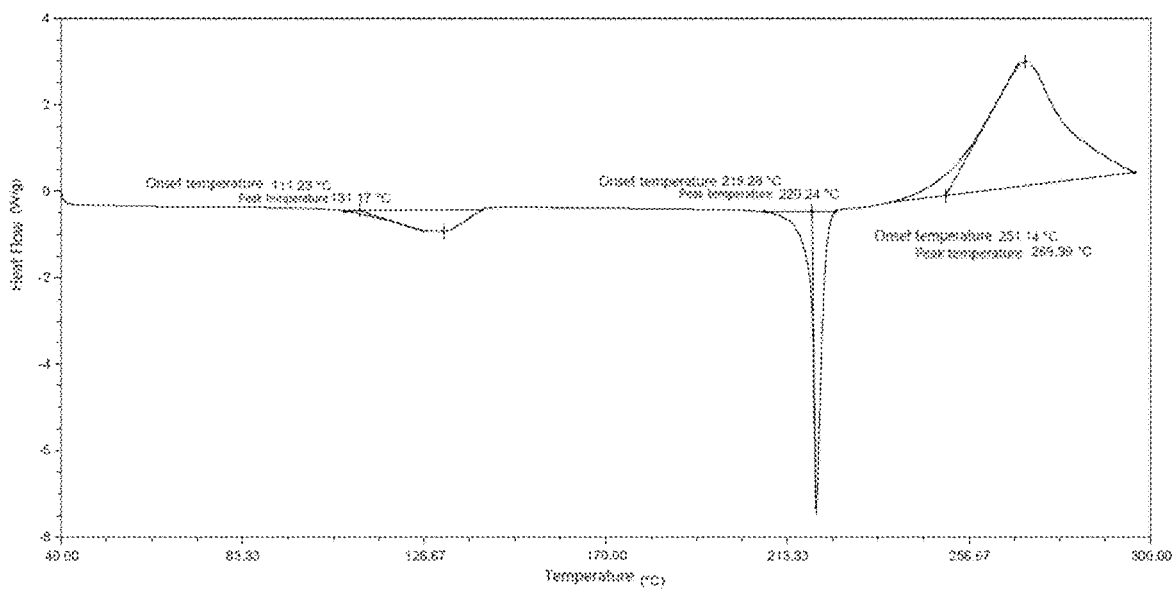
FIG. 2 illustrates a DSC pattern of the crystalline form D.
Figure 3:
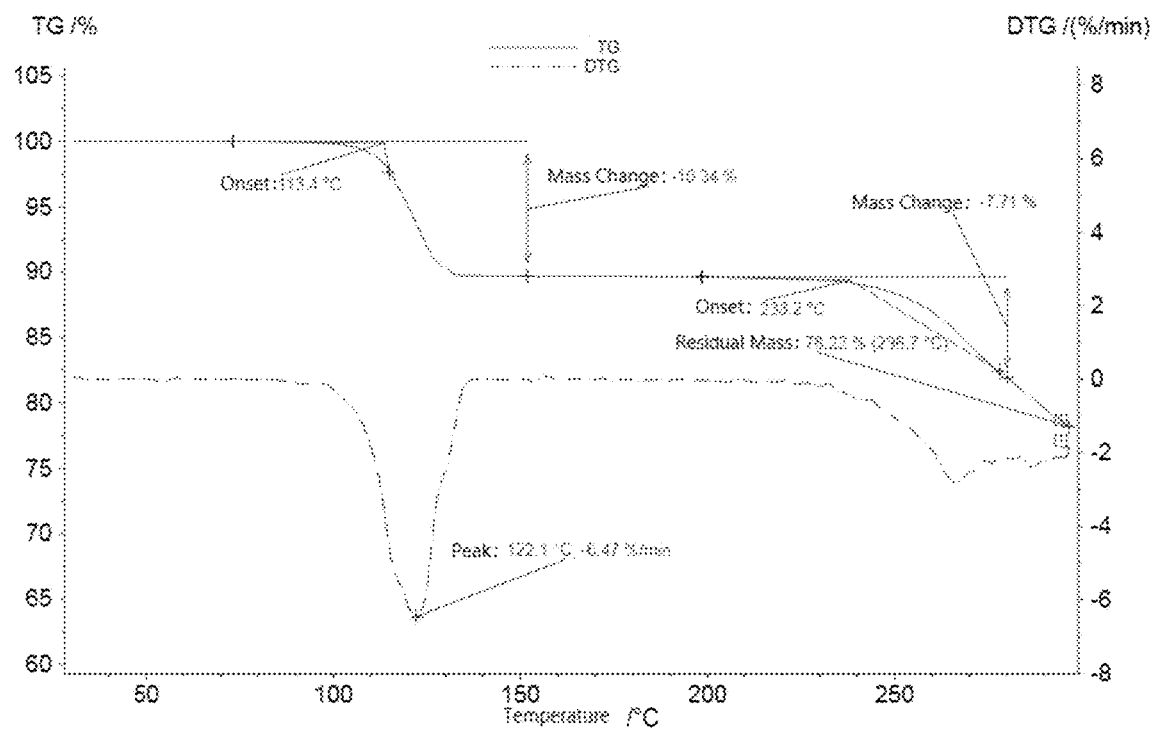
FIG. 3 illustrates a TG-DTG pattern of the crystalline form D.

An excessive amount of the compound of formula I was subjected to suspension crystallization at 25° C.: the compound was mixed with 2 mL of solvent n-hexanol, the mixture was stirred for equilibration for 24 h and centrifuged, and the solids were dried at 50° C. for 10 min to obtain the crystalline form D. Using Cu-Kα radiation, the X-ray powder diffraction (XRD) pattern is shown in FIG. 1, the differential scanning calorimetric (DSC) pattern is shown in FIG. 2 and the thermogravimetric-differential thermogravimetric (TG-DTG) pattern was shown in FIG. 3. The solvent was removed at 113.4° C. with a weight loss of about 10.34 wt %. The melting point after dehydration was $T_{onset}$=219.28° C., the transition did not occur before melting, and the decomposition started at about 251.14° C.

Example 2. Preparation of Crystalline Form E of Compound of Formula I

Example 2.1. Preparation of Crystalline Form E of Compound of Formula I

Figure 4:
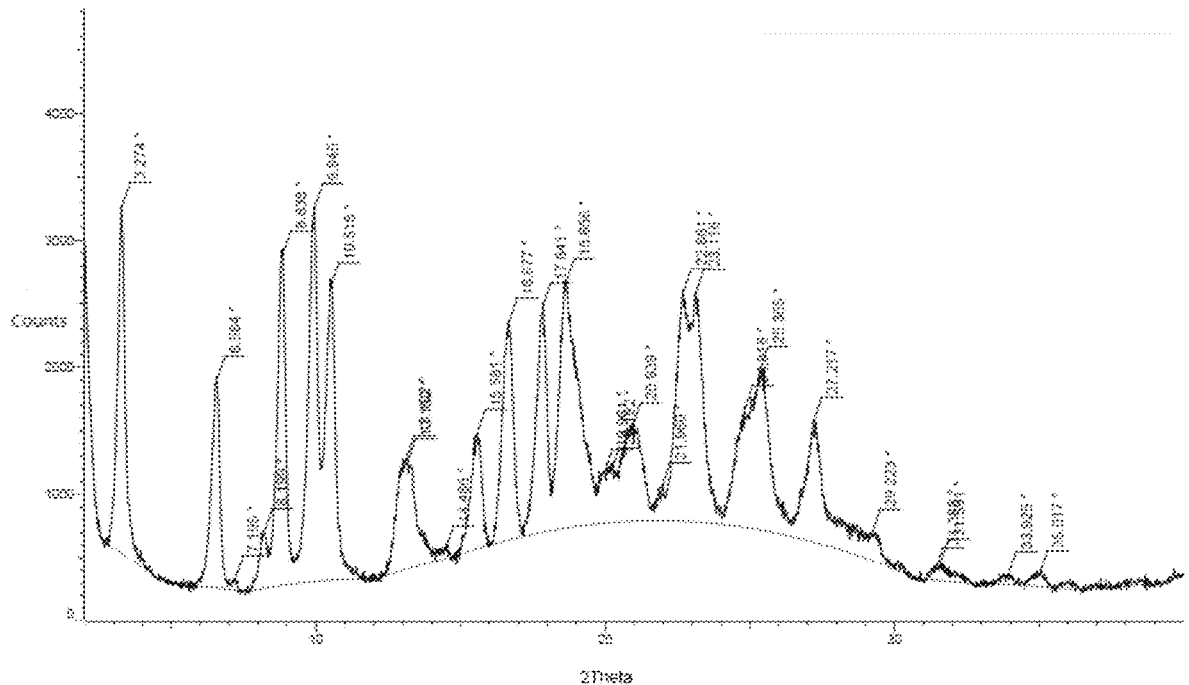
FIG. 4 illustrates an XRD pattern of the crystalline form E.
Figure 5:
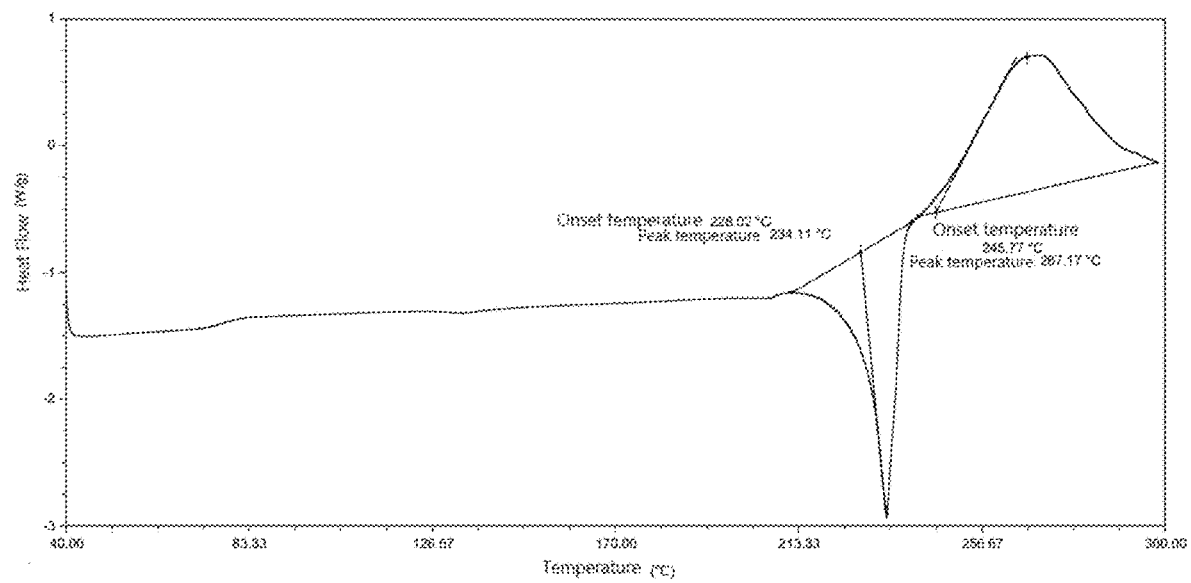
FIG. 5 illustrates a DSC pattern of the crystalline form E.
Figure 6:
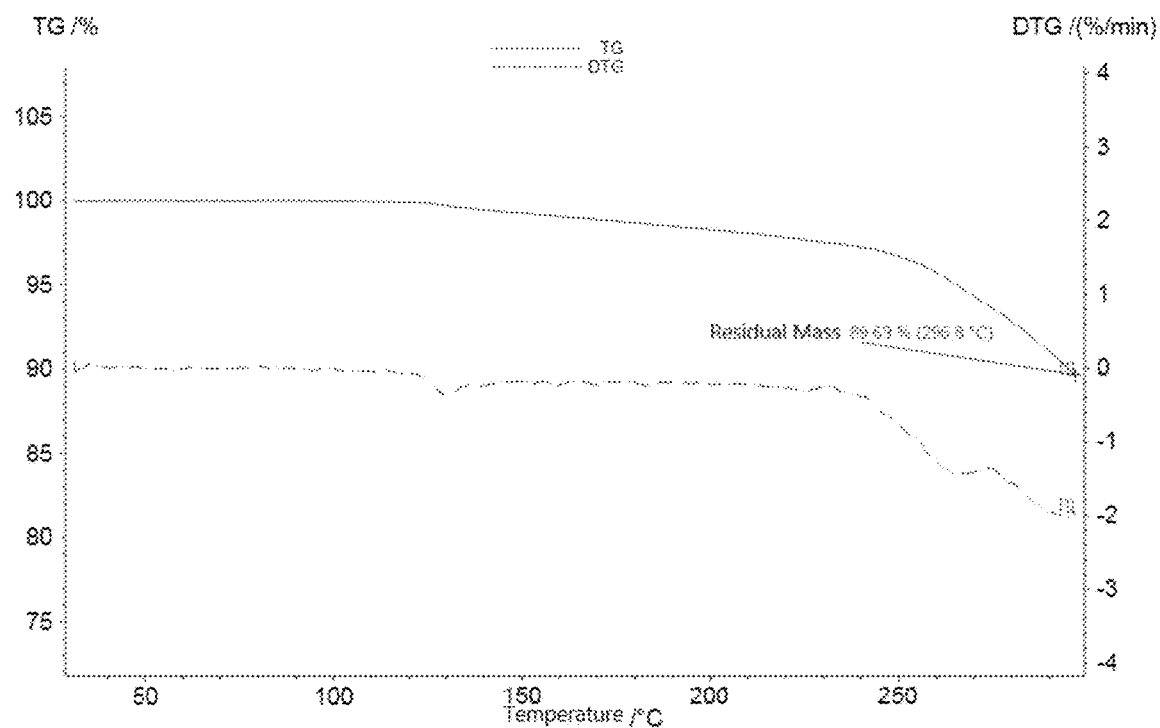
FIG. 6 illustrates a TG-DTG pattern of the crystalline form E.

A proper amount of the compound of formula I was dissolved in 5-10 mL of solvent paraxylene, and the mixture was heated to and stirred at 60° C. until the compound was completely dissolved; if not, the mixture was filtered to obtain a clear solution. The solution was cooled to 15° C. for crystallization and filtered. The residues were collected and dried to obtain the crystalline form E. Using Cu-Kα radiation, the X-ray powder diffraction (XRD) pattern is shown in FIG. 4, the differential scanning calorimetric (DSC) pattern is shown in FIG. 5 and the thermogravimetric-differential thermogravimetric (TG-DTG) pattern is shown in FIG. 6. The melting point of the crystalline form $T_{onset}$=228.02° C.

Example 2.2. Preparation of Crystalline Form E of Compound of Formula I

A proper amount of the compound of formula I was subjected to suspension crystallization at 25° C.: the compound was mixed with 2 mL of solvent paraxylene, the mixture was stirred for equilibration for 24 h and centrifuged, and the solids were dried at 50° C. for 10 min to obtain the crystalline form E.

Example 3. Preparation of Crystalline Form F of Compound of Formula I

Figures 7, 8:
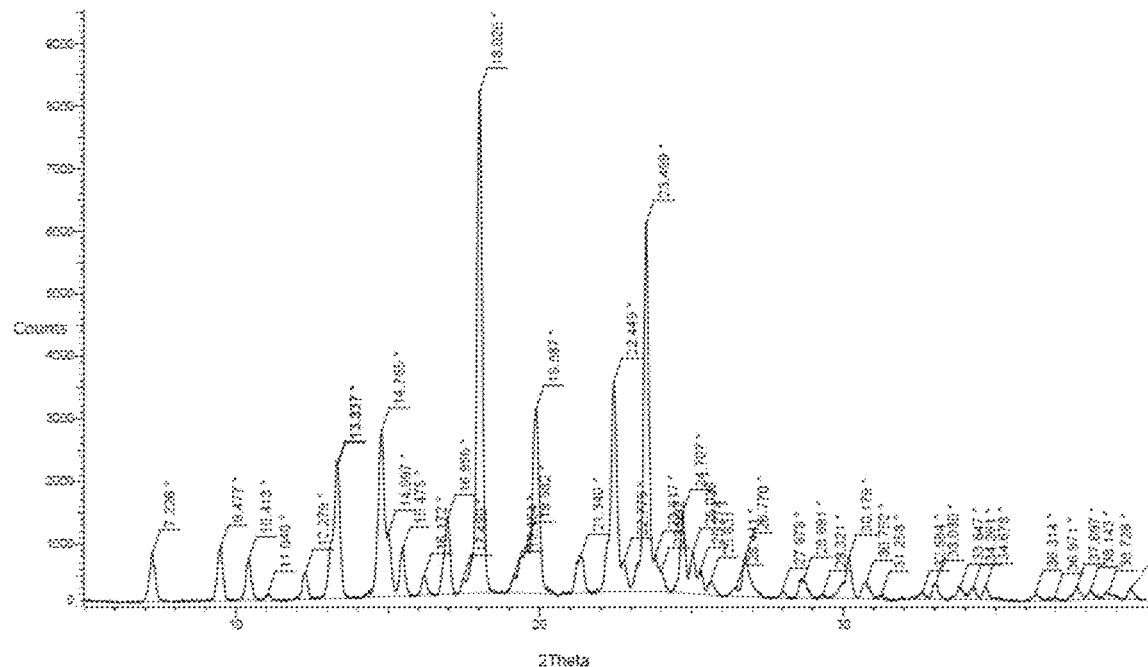
FIG. 7 illustrates an XRD pattern of the crystalline form F.
FIG. 8 illustrates a DSC pattern of the crystalline form F.
Figure 9:
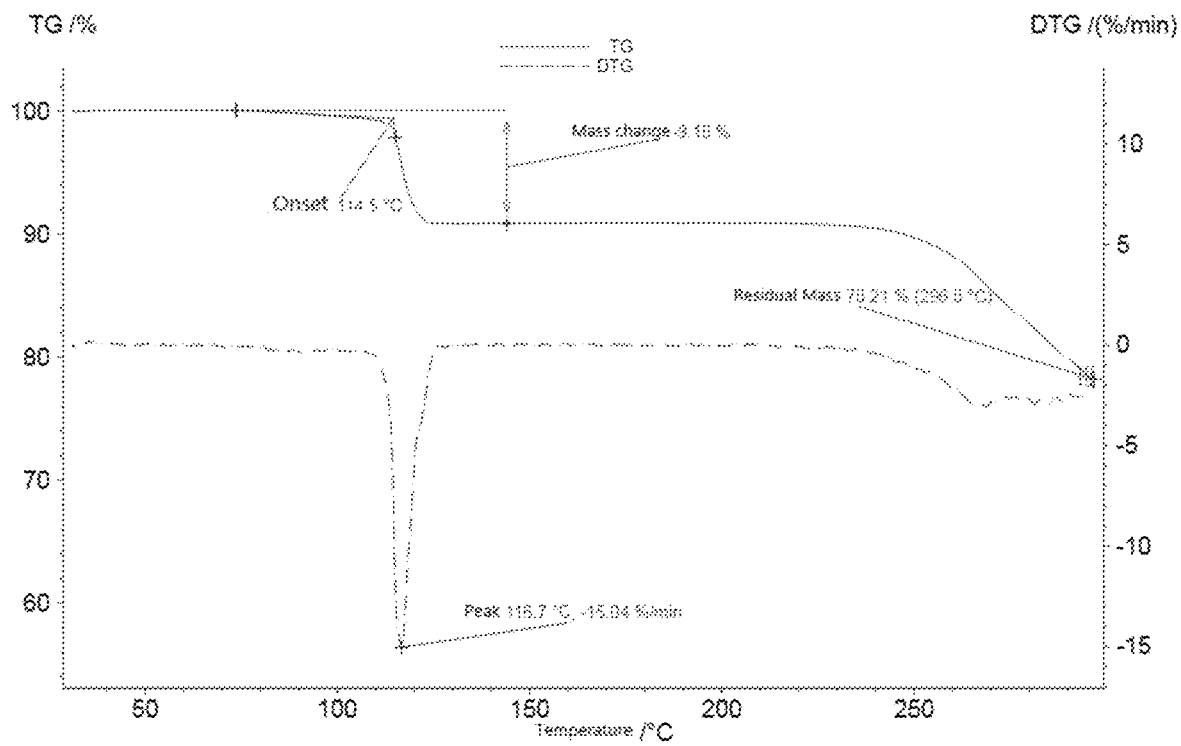
FIG. 9 illustrates a TG-DTG pattern of the crystalline form F.

A proper amount of the compound of formula I was subjected to suspension crystallization at 25° C.: the compound was mixed with 2 mL of solvent dioxane, the mixture was stirred for equilibration for 24 h and centrifuged, and the solids were dried at 50° C. for 10 min to obtain the crystalline form E Using Cu-Kα radiation, the X-ray powder diffraction (XRD) pattern is shown in FIG. 7, the differential scanning calorimetric (DSC) pattern is shown in FIG. 8 and the thermogravimetric-differential thermogravimetric (TG-DTG) pattern is shown in FIG. 9. The solvent was removed at 114.5° C. with a weight loss of about 9.18 wt %. The melting point after solvent removal was $T_{onset}$=219.88° C.

Example 4. Preparation of Crystalline Form G of Compound of Formula I

Example 4.1. Preparation of Crystalline Form G of Compound of Formula I

Figure 10:
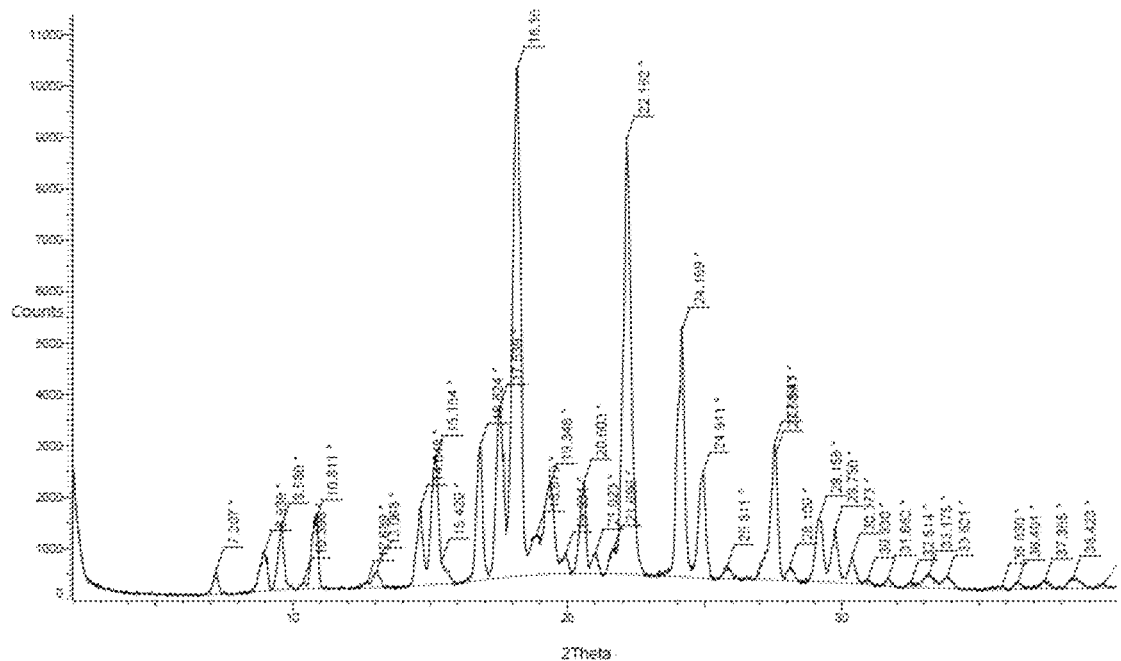
FIG. 10 illustrates an XRD pattern of the crystalline form G.
Figure 11:
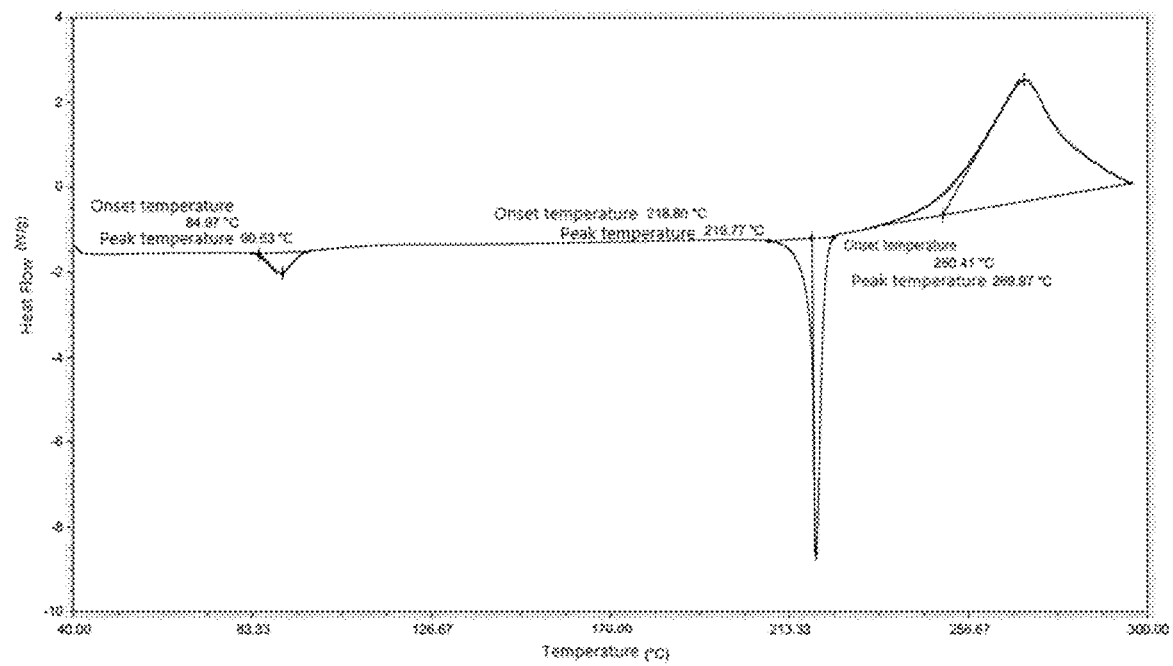
FIG. 11 illustrates a DSC pattern of the crystalline form G.
Figure 12:
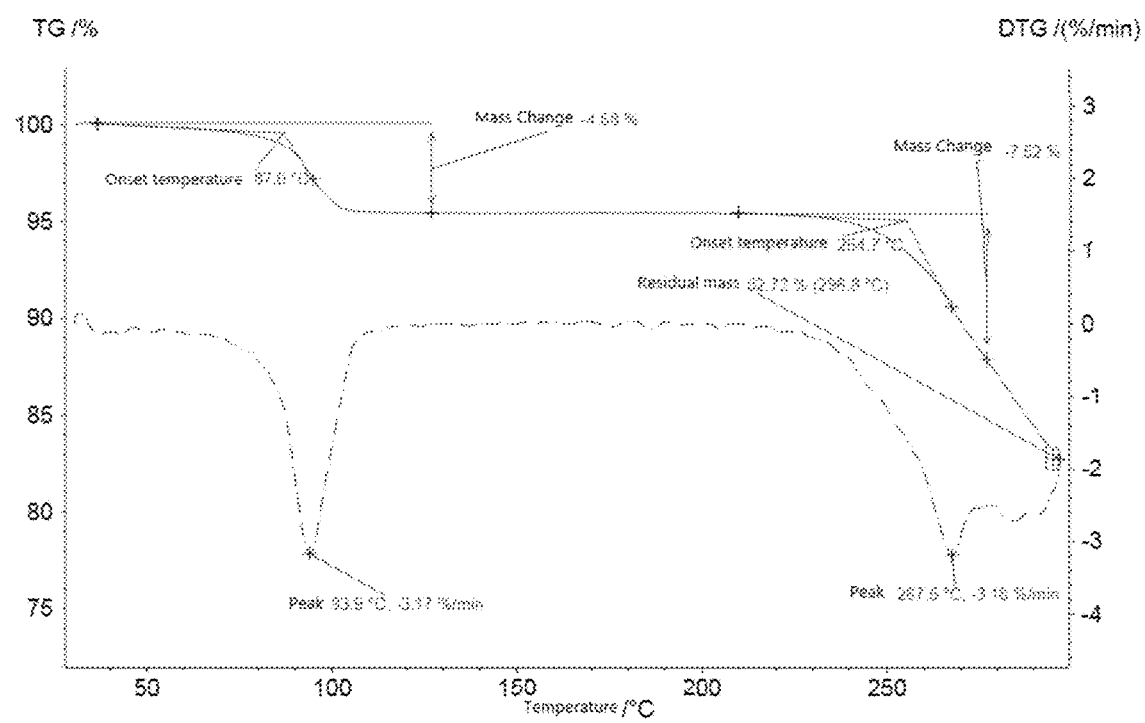
FIG. 12 illustrates a TG-DTG pattern of the crystalline form G.

A proper amount of the compound of formula I was subjected to suspension crystallization at 25° C.: the compound was mixed with 2 mL of solvent acetone, the mixture was stirred for equilibration for 24 h and centrifuged, and the solids were dried at 50° C. for 10 min to obtain the crystalline form G. Using Cu-Kα radiation, the X-ray powder diffraction (XRD) pattern is shown in FIG. 10, the differential scanning calorimetric (DSC) pattern is shown in FIG. 11 and the thermogravimetric-differential thermogravimetric (TG-DTG) pattern is shown in FIG. 12. The solvent was removed at 87.0° C. with a weight loss of about 4.68 wt %. The melting point after solvent removal was $T_{onset}$=218.80° C.

Example 4.2. Preparation of Crystalline Form G of Compound of Formula I

A proper amount of the compound of formula I was dissolved in solvent acetone, and the mixture was heated to and stirred at 45° C. until the compound was completely dissolved; if not, the mixture was filtered to obtain a clear solution. The clear solution was then transferred into a sample bottle, the solvent was slowly evaporated at room temperature for crystallization, and the residues were collected and dried to obtain the crystalline form G.

Example 5. Preparation of Crystalline Form H of Compound of Formula I

Figure 13:
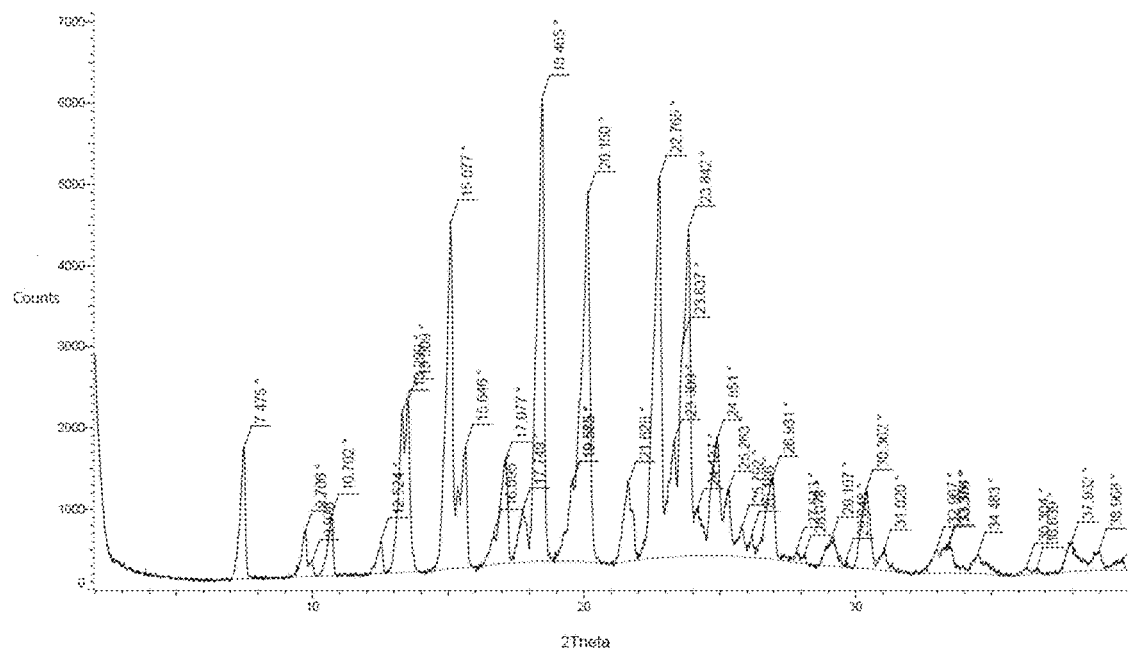
FIG. 13 illustrates an XRD pattern of the crystalline form H.
Figure 14:
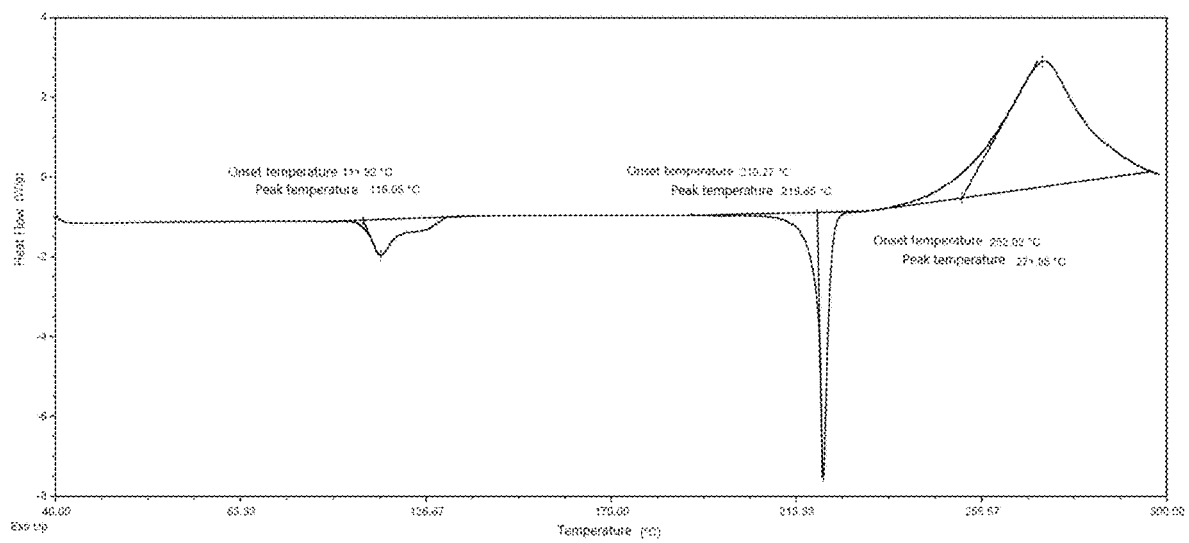
FIG. 14 illustrates a DSC pattern of the crystalline form H.
Figure 15:
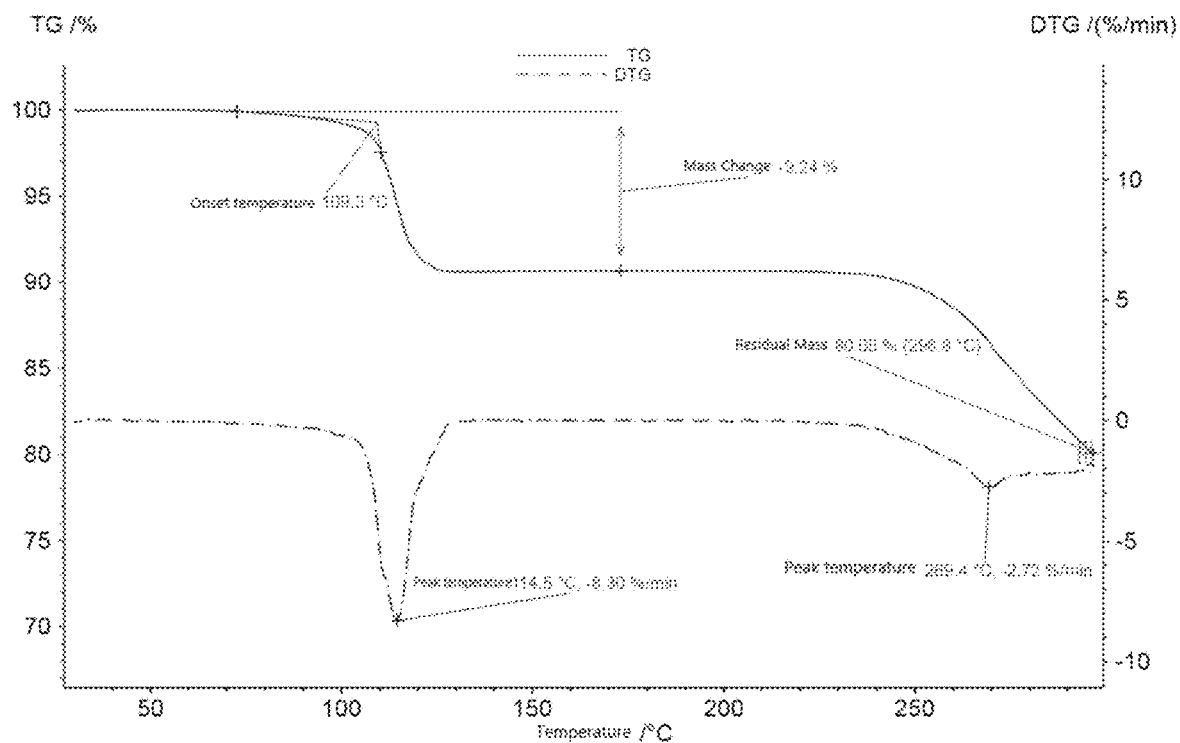
FIG. 15 illustrates a TG-DTG pattern of the crystalline form H.

A proper amount of the compound of formula I was dissolved in solvent ethyl acetate. The mixture was stirred for 24 hours and centrifuged. The solid was dried at 45° C. for 2 hours to obtain the crystalline form H. Using Cu-Kα radiation, the X-ray powder diffraction (XRD) pattern is shown in FIG. 13, the differential scanning calorimetric (DSC) pattern is shown in FIG. 14 and the thermogravimetric-differential thermogravimetric (TG-DTG) pattern is shown in FIG. 15. The solvent was removed at 109.3° C. with a weight loss of about 9.24 wt %. The melting point of the crystalline form $T_{onset}$=218.27° C.

Example 6. Preparation of Crystalline Form J of Compound of Formula I

Figure 16:
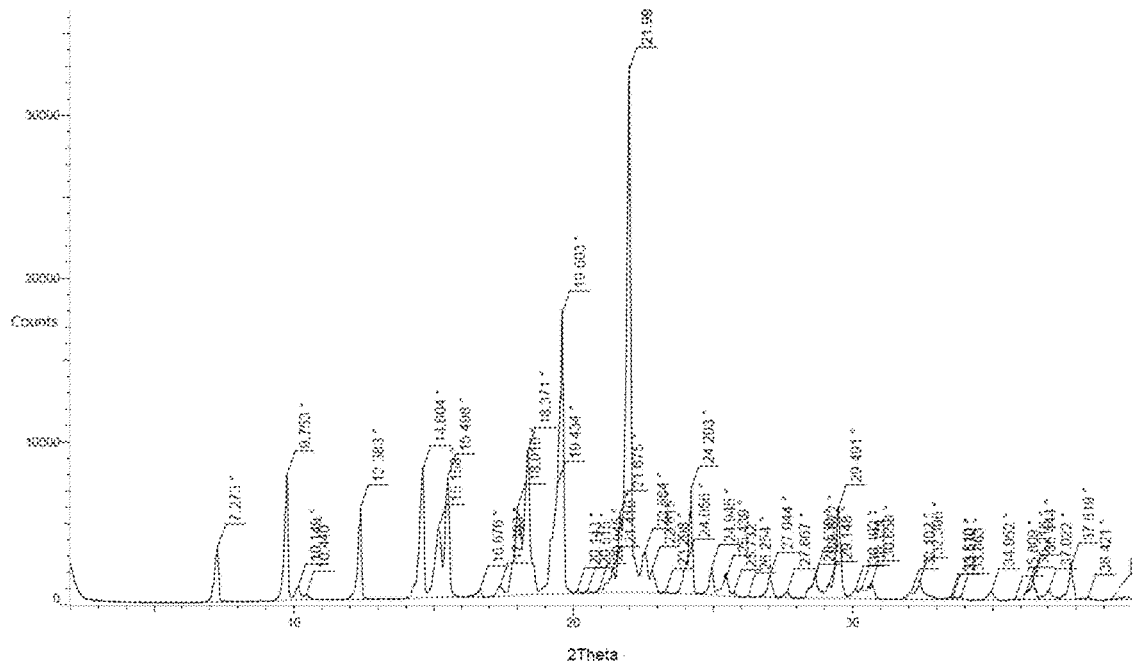
FIG. 16 illustrates an XRD pattern of the crystalline form J.
Figure 17:
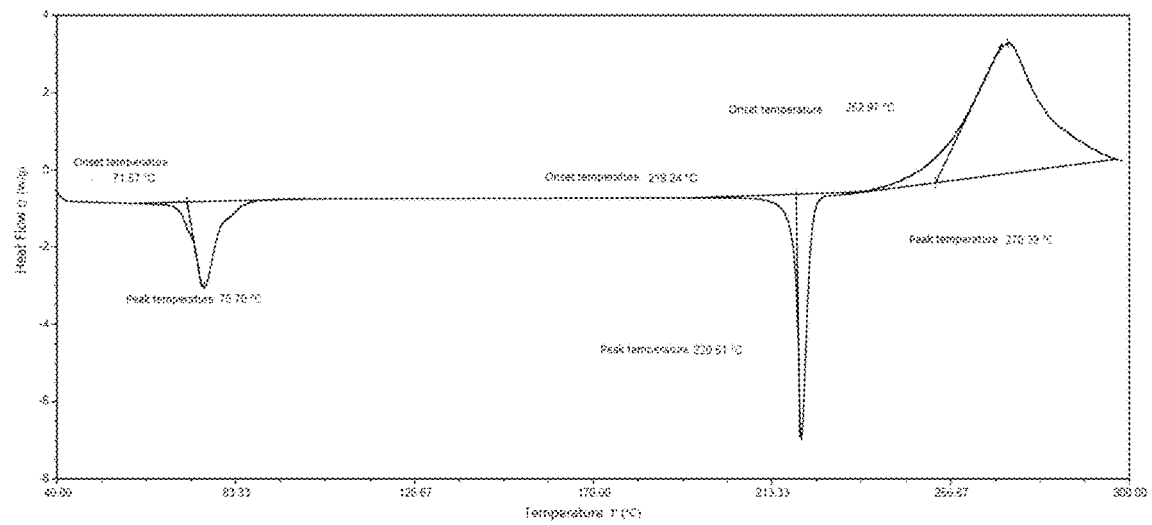
FIG. 17 illustrates a DSC pattern of the crystalline form J.
Figure 18:
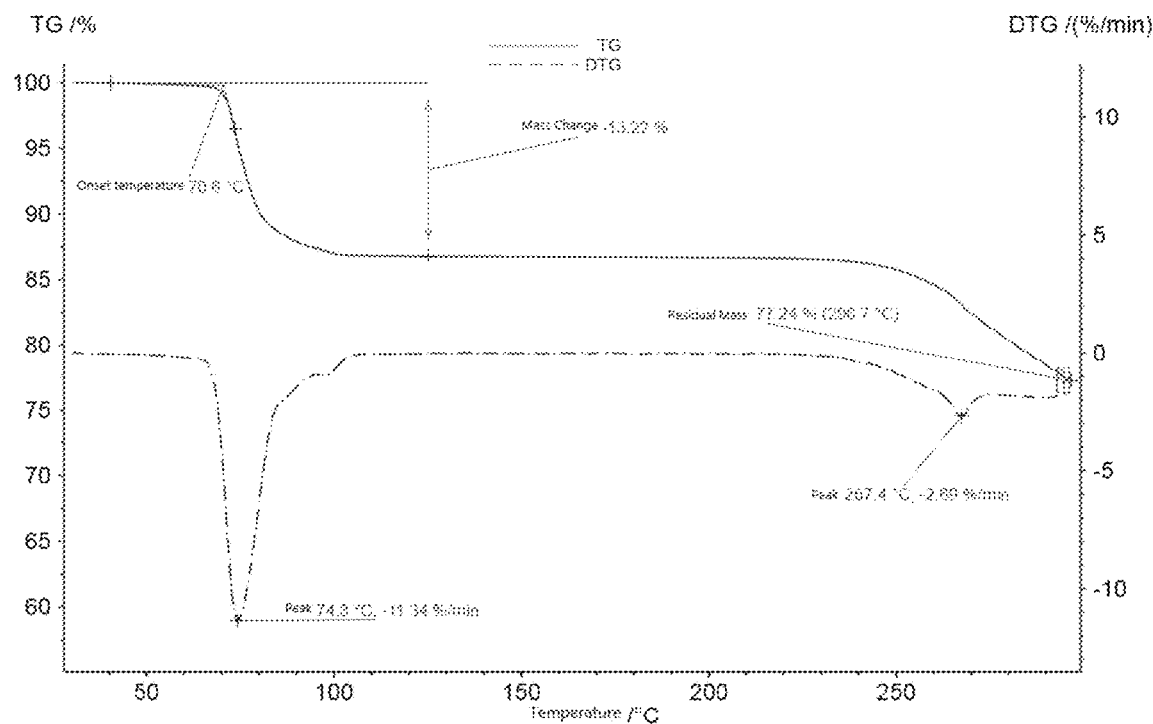
FIG. 18 illustrates a TG-DTG pattern of the crystalline form J.

A proper amount of the compound of formula I was dissolved in solvent tetrahydrofuran. The mixture was stirred for 24 hours and centrifuged. The solid was dried at 45° C. for 2 hours to obtain the crystalline form J. Using Cu-Kα radiation, the X-ray powder diffraction (XRD) pattern is shown in FIG. 16, the differential scanning calorimetric (DSC) pattern is shown in FIG. 17 and the thermogravimetric-differential thermogravimetric (TG-DTG) pattern is shown in FIG. 18. The solvent was removed at 70.6° C. with a weight loss of about 13.22 wt %. The melting point of the crystalline form $T_{onset}$=219.24° C.

Example 7. Stability in Solutions

Proper amounts of the solid samples obtained in Example 1, Example 2.1, Example 3, Example 4.1, Example 5 and Example 6 were dissolved in 2 mL of methanol, ethanol, acetone, acetonitrile, tetrahydrofuran, ethyl acetate, dioxane or water in 4-mL sample bottles by ultrasonication until a supersaturation state was reached. The mixtures were stirred at 20° C. for 24 hours and centrifuged, and the solids were dried at 45° C. for 2 hours. X-ray powder diffraction (XRD) spectroscopy was performed.

In the above test, the crystalline forms demonstrated the following results: stable and no crystalline form transition.

Example 8. Stability of Solids

According to the "Guidelines for the Stability Test of APIs and Preparations" (General Chapter 9001 in the Chinese Pharmacopoeia, Volume IV, 2015 Edition), the stabilities of the crystalline form D, the crystalline form E, the crystalline form F, the crystalline form G, the crystalline form H and the crystalline form J of the compound of formula I were investigated at high temperature (60° C., open), high humidity (room temperature/relative humidity 92.5%, open) and illumination (total illuminance of $1.2 \times 10^6$ Lux·hr/near UV energy of 200 w·hr/m², open).

5 mg of solid samples obtained in Example 1, Example 2.1, Example 3, Example 4.1, Example 5 and Example 6 were dispersed at the bottom of glass sample bottles as a thin layer. The vials in which the samples were placed at high temperature and high humidity were sealed with aluminum foil, and small holes were provided in the aluminum foil to ensure that the samples were sufficiently contacted with atmospheric air. The vial in which the sample was placed under strong light was placed open without sealing with aluminum foil. The samples placed in different conditions were taken and tested by XRD spectroscopy on day 5 and day 10. The test results were compared with the baseline on day 0.

Example 9. Hygroscopicity

Proper amounts of the solid samples obtained in Example 1, Example 2.1, Example 3, Example 4.1, Example 5 and Example 6 were subjected to dynamic vapor sorption (DVS) using a DVS Intrinsic dynamic vapor sorption system. The test temperature was 25° C., the relative humidity range was 0-95%, and the step size was 10%. The change in percentage weight gain of the sample with the relative humidity was investigated. X-ray powder diffraction (XRD) patterns of the sample were obtained, and the XRD patterns before and after the DVS test were compared.

Example 10. Powder Fluidity

Angle of repose: the included angle between the free surface of a powder pile in a static state and the horizontal plane. The experiment was performed using a powder flow analyzer. Proper amounts of the solid samples obtained in Example 1, Example 2.1, Example 3, Example 4.1, Example 5 and Example 6 were allowed to fall freely to form piles on a sample disk having a diameter of 25 cm, and then the heights of the piles were measured to calculate the powder angle of repose.

The invention claimed is:

1. A crystalline form of a compound of formula I or a solvate thereof, characterized by an X-ray powder diffraction pattern using Cu-Kα radiation, comprising diffraction peaks at 2θ in degree of 3.27±0.2°, 6.56±0.2°, 8.84±0.2°, 9.95±0.2°, 10.52±0.2°, 13.10±0.2°, 13.15±0.2°, 15.58±0.2°, 16.68±0.2°, 17.84±0.2° and 18.66±0.2°;
or the solvate of the compound of formula I is an n-hexanol solvate of the compound of formula I, and a crystalline form of the n-hexanol solvate is characterized by an X-ray powder diffraction pattern using Cu-Kα radiation, comprising diffraction peaks at 2θ in degree of 7.28±0.2°, 9.49±0.2°, 10.07±0.2°, 12.69±0.2°, 14.97±0.2°, 18.72±0.2°, 19.26±0.2°, 22.25±0.2°, 22.58±0.2° and 24.02±0.2°;
or the solvate of the compound of formula I is a dioxane solvate of the compound of formula I, and a crystalline form of the dioxane solvate is characterized by an X-ray powder diffraction pattern using Cu-Kα radiation, comprising diffraction peaks at 2θ in degree of 7.23±0.2°, 9.48±0.2°, 10.41±0.2°, 13.34±0.2°, 14.79±0.2°, 18.03±0.2°, 19.89±0.2°, 22.45±0.2° and 23.50±0.2°;
or the solvate of the compound of formula I is an acetone solvate of the compound of formula I, and a crystalline form of the acetone solvate is characterized by an X-ray powder diffraction pattern using Cu-Kα radiation, comprising diff action peaks at 2θ in degree of 7.21±0.2°, 8.94±0.2°, 9.58±0.2°, 10.81±0.2°, 14.65±0.2°, 15.18±0.2°, 16.82±0.2°, 17.54±0.2°, 18.16±0.2°, 19.93±0.2°, 20.60±0.2°, 22.16±0.2°, 24.17±0.2°, 24.91±0.2°, 27.54±0.2° and 27.59±0.2°; or the solvate of the compound of formula I is an ethyl acetate solvate of the compound of formula I, and a crystalline form of the ethyl acetate solvate is characterized by X-ray powder diffraction pattern using Cu-Kα radiation, comprising diffraction peaks at 2θ in degree of 7.48±0.2°, 9.71±0.2°, 10.70±0.2°, 12.52±0.2°, 13.30±0.2°, 13.51±0.2°, 15.08±0.2°, 15.65±0.2°, 17.08±0.2°, 18.47±0.2°, 20.15±0.2°, 21.63±0.2°, 22.77±0.2° and 23.84±0.2°;
or the solvate of the compound of formula I is a tetrahydrofuran solvate of the compound of formula I, and a crystalline form of the tetrahydrofuran solvate is characterized by an X-ray powder diffraction pattern using Cu-Kα radiation, comprising diffraction peaks at 2θ in degree of 7.27±0.2°, 9.75±0.2°, 10.15±0.2°, 10.44±0.2°, 12.38±0.2°, 14.60±0.2°, 15.16±0.2°, 15.50±0.2°, 18.01±0.2°, 18.37±0.2°, 19.60=0.2°, 21.99±0.2°, 24.20±0.2° and 29.49±0.2°.

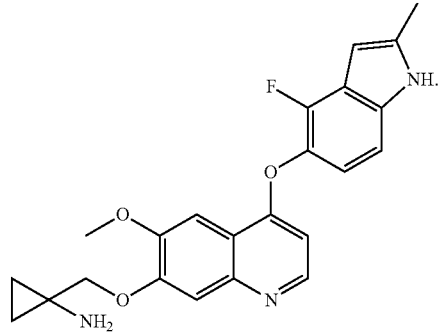

Formula I

2. The crystalline form of the compound of formula I or the solvate thereof of claim 1, wherein the crystalline form of the n-hexanol solvate is characterized by an X-ray powder diffraction pattern using Cu-Kα radiation, comprising diffraction peaks at 2θ in degree of 7.28±0.2°, 9.49±0.2°, 10.07±0.2°, 12.37±0.2°, 12.69±0.2°, 14.97±0.2°, 15.66±0.2°, 16.29±0.2°, 17.25=0.2°, 18.24=0.2°, 18.72=0.2°, 19.26±0.2°, 21.15=0.2°, 22.25±0.2°, 22.58±0.2° and 24.02±0.2°.

3. The crystalline form of the compound of formula I or the solvate thereof of claim 1, wherein the crystalline form of a compound of formula I is characterized by an X-ray powder diffraction pattern using Cu-Kα radiation, comprising diffraction peaks at 2θ in degree of 3.27±0.2°, 6.56=0.2°, 8.20±0.2°, 8.84±0.2°, 9.95±0.2°, 10.52±0.2°, 13.10±0.2°, 13.15±0.2°, 15.58±0.2°, 16.68±0.2°, 17.84±0.2°, 18.66±0.2°, 19.96=0.29 20.19±0.2°, 22.68±0.2°, 23.12±0.2°, 24.82±0.2°, 25.37±0.2° and 27.22±0.2°.

4. The crystalline form of the compound of formula I or the solvate thereof of claim 3, wherein the crystalline form of a compound of formula I is characterized by an X-ray powder diffraction pattern using Cu-Kα radiation, comprising diffraction peaks at 2θ in degree of 3.27+0.2°, 6.56±0.2°, 7.20±0.2°, 8.20±0.2°, 8.84±0.2°, 9.95±0.2°, 10.52±0.2°, 13.10±0.2°, 13.15±0.2°, 14.47±0.2°, 15.58±0.2°, 16.68±0.2°, 17.84±0.2°, 18.66±0.2°, 19.96±0.2°, 20.19±0.2°, 20.94±0.2°, 21.96±0.2°, 22.68±0.2°, 23.12±0.2°, 24.82±0.2°, 25.37±0.2°, 27.22±0.2°, 29.22±0.2°, 31.39±0.2°, 31.59±0.2°, 33.93±0.2° and 35.02±0.2°.

5. The crystalline form of the compound of formula I or the solvate thereof of claim 1, wherein the crystalline form of the dioxane solvate is characterized by an X-ray powder diffraction pattern using Cu-Kα radiation, comprising diffraction peaks at 2θ in degree of about 7.23±0.2°, 9.48±0.2°, 10.41±0.2°, 11.04±0.2°, 12.28±0.2°, 13.34±0.2°, 14.79±0.2°, 15.00=0.2°, 15.48±0.2°, 16.17±0.2°, 16.96±0.2°, 17.49±0.2°, 18.03=0.29 19.58±0.2°, 19.89±0.2°, 21.34±0.2°, 22.45±0.2°, 23.50±0.2°, 24.71±0.2°, 25.04±0.2°, 26.77±0.2° and 30.18±0.2°.

6. The crystalline form of the compound of formula I or the solvate thereof of claim 1, wherein the crystalline form of the acetone solvate is characterized by an X-ray powder diffraction pattern using Cu-Kα radiation, comprising diffraction peaks at 2θ in degree of 7.21±0.2°, 8.94±0.2°, 9.58±0.2°, 10.81=0.2°, 13.07±0.2°, 14.65=0.2°, 15.18±0.2°, 16.82±0.2°, 17.54±0.2°, 18.16±0.2°, 18.88±0.2°, 19.93±0.2°, 20.60±0.2°, 21.02±0.2°, 22.16±0.2°, 24.17±0.2°, 24.91±0.2°, 25.81±0.2°, 27.54±0.2°, 27.59±0.2°, 29.16±0.2° and 29.75±0.2°.

7. The crystalline form of the compound of formula I or the solvate thereof of claim 1, wherein the crystalline form of the ethyl acetate solvate is characterized by an X-ray powder diffraction pattern using Cu-Kα radiation, comprising diffraction peaks at 2θ in degree of 7.48±0.2°, 9.71=0.2°, 9.98±0.2°, 10.70±0.2°, 12.52±0.2°, 13.30±0.2°, 13.51±0.2°, 15.08±0.2°, 15.65±0.2°, 17.08±0.2°, 17.75=0.2°, 18.47±0.2°, 19.57±0.2°, 20.15±0.2°, 21.63±0.2°, 22.77±0.2°, 23.31±0.2°, 23.84±0.2°, 24.85±0.2°, 25.26=0.2°, 25.79±0.2°, 26.19±0.2°, 26.93±0.2°, 29.11±0.2°, 29.65±0.2° and 30.36±0.2°.

8. The crystalline form of the compound of formula I or the solvate thereof of claim 1, wherein the crystalline form of the tetrahydrofuran solvate is characterized by an X-ray powder diffraction pattern using Cu-Kα radiation, comprising diffraction peaks at 2θ in degree of 7.27±0.2°, 9.75±0.2°, 12.38±0.2°, 14.60±0.2°, 15.16±0.2°, 15.50±0.2°, 18.01±0.2°, 18.37±0.2°, 19.60=0.2°, 21.68±0.2°, 21.99=0.2°, 22.56±0.2°, 22.82±0.2°, 24.20±0.2°, 24.95±0.2°, 25.44±0.2°, 27.04±0.2°, 27.67±0.2°, 28.67±0.2°, 29.15±0.2°, 29.49±0.2° and 37.82±0.2°.

9. The crystalline form of the compound of formula I or the solvate thereof of claim 1, wherein the crystalline form of a compound of formula I is characterized by an X-ray powder diffraction pattern using Cu-Kα radiation, and the XRD pattern of the crystalline form E is as shown in FIG. 4.

10. The crystalline form of the compound of formula I or the solvate thereof of claim 1, wherein the crystalline form of a compound of formula I is characterized by an X-ray powder diffraction pattern using Cu-Kα radiation, comprising diffraction peaks at 2θ in degree in the following Table:

| Serial number | 2θ (°) | Relative intensity (%) |
|---|---|---|
| 1 | 3.27 | 92.7 |
| 2 | 6.56 | 55.5 |
| 3 | 7.20 | 2.9 |
| 4 | 8.20 | 15.0 |
| 5 | 8.84 | 88.3 |
| 6 | 9.95 | 100.0 |
| 7 | 10.52 | 78.5 |
| 8 | 13.10 | 29.3 |
| 9 | 13.15 | 28.4 |
| 10 | 14.47 | 2.4 |
| 11 | 15.58 | 30.7 |
| 12 | 16.68 | 58.1 |
| 13 | 17.84 | 60.1 |
| 14 | 18.66 | 65.5 |
| 15 | 19.96 | 13.2 |
| 16 | 20.19 | 13.5 |
| 17 | 20.94 | 25.1 |
| 18 | 21.96 | 9.0 |
| 19 | 22.68 | 61.0 |
| 20 | 23.12 | 60.9 |
| 21 | 24.82 | 31.4 |
| 22 | 25.37 | 42.5 |
| 23 | 27.22 | 32.2 |
| 24 | 29.22 | 7.3 |
| 25 | 31.39 | 2.3 |
| 26 | 31.59 | 4.8 |
| 27 | 33.93 | 2.4 |
| 28 | 35.02 | 3.2. |

11. The crystalline form of the compound of formula I or the solvate thereof of claim 1, wherein the crystalline form of the compound of formula I or the solvate thereof is present in a crystalline composition at 50% or more by weight of the crystalline composition.

12. The crystalline form of the compound of formula I or the solvate thereof of claim 1, wherein the crystalline form of the compound of formula I or the solvate thereof is present in a crystalline composition at 70% or more by weight of the crystalline composition.

13. The crystalline form of the compound of formula I or the solvate thereof of claim 1, wherein the crystalline form of the compound of formula I or the solvate thereof is present in a crystalline composition at 90% or more by weight of the crystalline composition.

14. The crystalline form of the compound of formula I or the solvate thereof of claim 1, wherein the crystalline form of the compound of formula I or the solvate thereof is present in a crystalline composition at 95% or more by weight of the crystalline composition.

15. A pharmaceutical composition comprising an effective amount of the crystalline form of the compound of formula I or the solvate thereof of claim 1 or the crystalline composition thereof, and one or more pharmaceutically acceptable carriers.

16. A method for treating a tumor, comprising administering to a subject in need a therapeutically effective amount of the crystalline form of the compound of formula I or the solvate thereof of claim 1, a crystalline composition comprising the same, or a pharmaceutical composition comprising the same, wherein the tumor is selected from the group consisting of:
 liver cancer,
 kidney cancer,
 colon cancer gastrointestinal stromal tumor,
 soft tissue sarcoma,
 gastric cancer,
 medullary thyroid cancer,
 esophageal squamous cell carcinoma,
 small-cell lung cancer,
 non-small cell lung cancer,
 endometrial cancer,
 ovarian cancer,
 cervical cancer, and
 fallopian tube cancer.

* * * * *